United States Patent
Suddaby

(10) Patent No.: US 10,188,428 B2
(45) Date of Patent: Jan. 29, 2019

(54) SUBCUTANEOUS IMPLANTABLE DEVICE FOR GRADUALLY ALIGNING A SPINE

(71) Applicant: Loubert S. Suddaby, Orchard Park, NY (US)

(72) Inventor: Loubert S. Suddaby, Orchard Park, NY (US)

( * ) Notice: Subject to any disclaimer, the term of this patent is extended or adjusted under 35 U.S.C. 154(b) by 0 days.

(21) Appl. No.: 15/595,292

(22) Filed: May 15, 2017

(65) Prior Publication Data

US 2018/0325557 A1    Nov. 15, 2018

(51) Int. Cl.
| | |
|---|---|
| A61B 17/70 | (2006.01) |
| A61B 17/88 | (2006.01) |
| A61M 25/04 | (2006.01) |
| A61B 17/56 | (2006.01) |
| A61B 17/00 | (2006.01) |
| A61B 17/68 | (2006.01) |

(52) U.S. Cl.
CPC ...... *A61B 17/7022* (2013.01); *A61B 17/8869* (2013.01); *A61M 25/04* (2013.01); *A61B 2017/00004* (2013.01); *A61B 2017/564* (2013.01); *A61B 2017/681* (2013.01)

(58) Field of Classification Search
CPC ............ A61B 17/7053; A61B 17/7022; A61B 17/8861; A61B 17/8869
See application file for complete search history.

(56) References Cited

U.S. PATENT DOCUMENTS

| | | | |
|---|---|---|---|
| 5,782,831 A | 7/1998 | Sherman et al. | |
| 6,551,320 B2 | 4/2003 | Lieberman | |
| 8,357,183 B2 * | 1/2013 | Seme | A61B 17/7001 606/257 |
| 8,764,803 B2 * | 7/2014 | Suddaby | A61B 17/88 606/263 |
| 8,828,058 B2 * | 9/2014 | Elsebaie | A61B 17/7001 606/258 |
| 9,333,009 B2 * | 5/2016 | Kroll | A61B 17/7014 |
| 9,408,638 B2 * | 8/2016 | Kroll | A61B 17/7014 |
| 9,895,168 B2 * | 2/2018 | Kroll | A61B 17/7014 |
| 9,968,379 B2 * | 5/2018 | Suddaby | A61B 17/7053 |
| 2006/0195090 A1 | 8/2006 | Suddaby | |
| 2008/0023012 A1 * | 1/2008 | Dineen | A61B 17/0401 128/848 |
| 2008/0183214 A1 * | 7/2008 | Copp | A61B 17/7005 606/265 |
| 2009/0012565 A1 * | 1/2009 | Sachs | A61B 17/7041 606/246 |

(Continued)

OTHER PUBLICATIONS https://www.nuvasive.com/procedures/spine/magec, last accessed Jun. 21, 2017.

*Primary Examiner* — Jacqueline T Johanas
(74) *Attorney, Agent, or Firm* — Simpson & Simpson, PLLC

(57) ABSTRACT

A subcutaneous implantable device for aligning a spine having a plurality of vertebrae, including a stabilizing plate assembly, a first rod, including a first end, and a second end coupled to the stabilizing plate assembly, a second rod, including a third end, and a fourth end coupled to the stabilizing plate assembly, a winding assembly, and a tensioning member including a line, the line having a first end, and a second end secured to the winding assembly, wherein the line is connected to the stabilizing plate assembly.

18 Claims, 23 Drawing Sheets

(56) References Cited

U.S. PATENT DOCUMENTS

| | | | |
|---|---|---|---|
| 2009/0112262 A1 | 4/2009 | Pool et al. | |
| 2010/0318129 A1* | 12/2010 | Seme | A61B 17/7001 606/254 |
| 2011/0054536 A1* | 3/2011 | Elsebaie | A61B 17/7001 606/264 |
| 2011/0066188 A1* | 3/2011 | Seme | A61B 17/7041 606/264 |
| 2012/0203282 A1* | 8/2012 | Sachs | A61B 17/7041 606/278 |
| 2013/0211455 A1* | 8/2013 | Seme | A61B 17/7001 606/257 |
| 2014/0236234 A1* | 8/2014 | Kroll | A61B 17/7014 606/264 |
| 2015/0196342 A1* | 7/2015 | Suddaby | A61B 17/8869 606/279 |
| 2015/0335360 A1* | 11/2015 | Seme | A61B 17/70 606/252 |
| 2016/0022323 A1* | 1/2016 | Seme | A61B 17/7041 606/263 |
| 2016/0128735 A1* | 5/2016 | Suddaby | A61B 17/66 606/263 |
| 2017/0189070 A1* | 7/2017 | Serbousek | A61B 17/7005 |

* cited by examiner

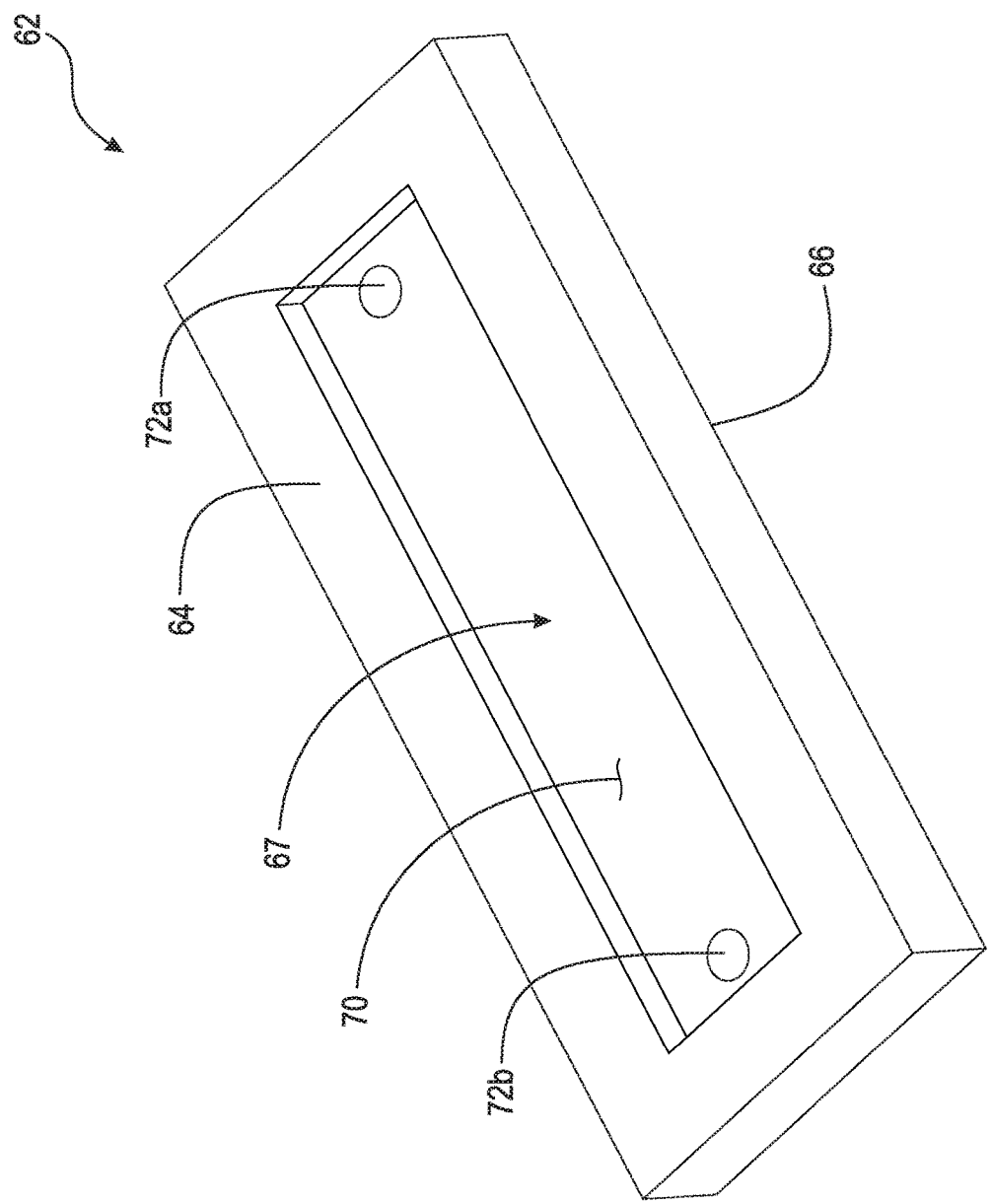

SUBCUTANEOUS IMPLANTABLE DEVICE FOR GRADUALLY ALIGNING A SPINE

FIELD

The present invention relates to surgical devices, and, more particularly, to orthopedic surgical devices, and, more particularly, to corrective orthopedic surgical devices related to the spine.

BACKGROUND

Scoliosis is a disorder that causes an abnormal curve of the spine, or backbone. Patients with scoliosis develop abnormal curves to either side of the body's median line (lateral curve) and the bones of the spine twist on each other like a corkscrew. Scoliosis is about two times more common in girls than boys. It can be seen at any age, but it is most common in those over ten years old.

FIG. 1 is a stylized posterior view of a person P with a spine afflicted with scoliosis. Spinal column 1 is shown to have two lateral curves—upper curve 2 and lower curve 3. Often the presence of one lateral curve generates the formation of a second curve to compensate for the reduced spinal support of the body caused by one lateral curve. FIGS. 2A and 2B depict two different types of prior art braces 4 and 5, respectively, used to prevent further deterioration of spinal alignment. In some cases, braces such as braces 4 and 5 may improve the condition, but they rarely enable the wearer to achieve a full recovery to a correct spinal alignment.

Often, the cause of scoliosis is unknown and is described based on the age when scoliosis develops. If the person is less than 3 years old, it is called infantile idiopathic scoliosis. Scoliosis that develops between 3 and 10 years of age is called juvenile idiopathic scoliosis, and people that are over 10 years old have adolescent idiopathic scoliosis.

In functional scoliosis, the spine is normal, but an abnormal curve develops because of a problem somewhere else in the body. This could be caused by one leg being shorter than the other or by muscle spasms in the back. In the neuromuscular form, there is a problem during the formation of the bones of the spine. Either the bones of the spine fail to form completely or they fail to separate from each other. This type of scoliosis may develop in people with other disorders including birth defects, muscular dystrophy, cerebral palsy, and Marfan's disease. This type of scoliosis is often much more severe and needs more aggressive treatment than other forms of scoliosis. Degenerative scoliosis occurs in older adults. It is caused by changes in the spine due to arthritis. Weakening of the normal ligaments and other soft tissues of the spine combined with abnormal bone spurs can lead to an abnormal curvature of the spine.

Adolescent idiopathic scoliosis is the most common form of scoliosis. If the angle of the spinal curve (Cobb's angle) is small when first diagnosed, it can be observed and followed with routine X-rays and measurements. If the curve stays below 25 degrees, no other treatment is usually needed. If the curve is between 25-40 degrees, the curve can be considered significant and a brace may be recommended. If the curve is greater than 40 degrees, the curve can be considered severe and surgery may be recommended. Braces are not designed to correct severe spinal curves. They are used to help slow or stop the curve from getting worse. Since surgery is recommended typically only when the curve is considered significant or severe, surgeons are limited to performing surgical procedures on a subset of the population of individuals diagnosed with scoliosis.

Spinal fusion is one surgical procedure that may be used to alleviate scoliosis. In this procedure, bone is grafted to the vertebrae to form a rigid column. The rigidity of the column prevents the curve from worsening. However, the rigid column reduces the range of motion available to the patient.

Modern surgical procedures attempt to address sagittal imbalance and rotational defects unresolved by the earlier rod systems. They primarily involve a combination of rods, screws, hooks, cables and/or wires fixing the spine and applying forces to the spine to correct the spinal curvature. An example of the use of screws and cables is seen in U.S. Patent Application Publication No. 2006/0195090 (Suddaby) which is hereby incorporated by reference in its entirety. Suddaby discloses a system for improving the alignment of a spine by placing a series of screws or pins into the posterior or lateral side of the bodies of individual vertebrae. Hollow spacers are placed between the pins and a cable is extended through the heads of the pins and the spacers and is attached to an expansion sleeve. Tension is applied to the cable by pulling it through the expansion sleeve and then applying tension to the cable to pull the attached pins into an improved alignment. One of a plurality of nodules at the end of the cable is then placed into the passage of the expansion sleeve thereby holding the cable in the new "tensioned" position. The tension discourages movement of the spine.

U.S. Pat. No. 6,551,320 (Lieberman) discloses an apparatus for aligning a spine that includes a plurality of anchors screwed into adjacent vertebral bodies. A cable or series of cables is strung through or around the anchors and then pulled. The tension applied to the cable(s) is used to pull the spine into a desired alignment. U.S. Patent Application Publication No. 2009/0112262 (Pool et al.) discloses a system in which at least one anchor is screwed or otherwise embedded into an upper vertebra and one or more anchors are similarly placed in lower vertebra(ae). A cable is extended between the anchors and force applied to the cable by a magnetic adjustment device to align the spine. In some cases a second anchor-cable arrangement can be used on the opposite side of the spine.

U.S. Pat. No. 5,782,831 (Sherman et al.) discloses a system for reducing a displaced vertebra between adjacent vertebrae. The Sherman patent describes a system in which two anchors are screwed into the vertebrae on either side of the displaced vertebra with a rod attached between the anchors. A third anchor is screwed into the displaced vertebra and attached to a cable. A cable tightening device, such as a come-along type device is used to pull the displaced vertebra into alignment after which it is attached to the support rod. However, the attachment of a bar across three adjacent vertebrae prevents pulling a curved spine into a more proper alignment.

In attempting to solve spinal alignment and displacement problems, the prior art relies on multiple vertebral anchors and the application of alignment force through complicated force applicators and cable systems. Such corrective systems can be prohibitively expensive. Additionally, typical corrective systems involve the risk of permanent neurological injury caused by stretching the spinal cord. Other typical risks of surgical corrective systems for treating scoliosis involve infection, blood loss, and lung, bowel, and bladder problems. Because direct visualization of the individual spinal elements is often required for the above techniques, lengthy incisions and large spinal dissections are required to expose the spinal segments requiring treatment. Even with these major life threatening surgeries, perfect spinal alignment is rarely, if ever, achieved.

A subcutaneous apparatus for aligning the spine is needed that possesses few parts and is easy to implant while enabling a gradual restoration of the spinal alignment over a determined period of time so that large and/or sudden forces are not applied to the curved spine. By applying reduced corrective forces over a longer period of time, complications such as bone fracture and nerve damage can be reduced or avoided. Moreover, it would be advantageous in the art of neurosurgery and orthopedic surgery to align a spine with simple subcutaneous methods so that endoscopic or minimally invasive techniques can be employed. Additionally, it would be advantageous to access a device for aligning a spine by palpating intact skin to avoid infections. Additionally, the subcutaneous design of the apparatus could reduce infections compared to percutaneous designs.

SUMMARY

According to aspects illustrated herein, there is provided a subcutaneous implantable device for aligning a spine having a plurality of vertebrae, comprising a stabilizing plate assembly, a first rod, including a first end, and a second end coupled to the stabilizing plate assembly, a second rod, including a third end, and a fourth end coupled to the stabilizing plate assembly, a winding assembly, and a tensioning member including a line, the line having a first end, and a second end secured to the winding assembly, wherein the line is connected to the stabilizing plate assembly.

According to aspects illustrated herein, there is provided a subcutaneous implantable device for aligning a spine having a plurality of vertebrae, comprising a first pivot connection secured to a first vertebra of the spine, a second pivot connection secured to a second vertebra of the spine, a stabilizing plate assembly secured to a rib, a first rod, including a first end pivotably secured to the first pivot connection, and a second end pivotably secured to the stabilizing plate assembly, a second rod, including a third end pivotably secured to the second pivot connection, and a fourth end pivotably secured to the stabilizing plate assembly, a ratchet assembly connected to a third vertebra of the spine, and a tensioning member, including an inflatable balloon anchor connected to a fourth vertebra of the spine, and a line connected to the inflatable balloon anchor at a proximal end and the ratchet assembly at a distal end, wherein the line is connected to the stabilizing plate assembly.

According to aspects illustrated herein, there is provided a subcutaneous implantable device for aligning a spine having a plurality of vertebrae, comprising a tensioning member, comprising an inflatable balloon anchor including a port, a line having a first end connected to the port, wherein material is injected through the line into the inflatable balloon anchor.

According to aspects illustrated herein, there is provided a method of securing a tensioning member for gradually aligning a spine to a vertebra of the spine, the tensioning member comprising an inflatable balloon anchor and a hollow tube connected at a first end to the inflatable balloon anchor, the method comprising tapping a cylindrical needle having first end across a lateral side of the vertebra until the first end protrudes from a contralateral side of the vertebra, inserting the inflatable balloon anchor through the cylindrical needle until the inflatable balloon anchor protrudes from the contralateral side, inflating the inflatable balloon anchor with a material, and removing the cylindrical needle.

These and other objects, features, and advantages of the present disclosure will become readily apparent upon a review of the following detailed description of the disclosure, in view of the drawings and appended claims.

BRIEF DESCRIPTION OF THE DRAWINGS

Various embodiments are disclosed, by way of example only, with reference to the accompanying schematic drawings in which corresponding reference symbols indicate corresponding parts, in which:

FIG. 8 is a top perspective view of the lower component shown in FIG. 6;

FIG. 15A depicts a first method of attaching an inflatable balloon anchor to the apex vertebra;

FIG. 16A depicts a second method of attaching an inflatable balloon anchor to the apex vertebra;

DETAILED DESCRIPTION

At the outset, it should be appreciated that like drawing numbers on different drawing views identify identical, or functionally similar, structural elements. It is to be understood that the claims are not limited to the disclosed aspects.

Furthermore, it is understood that this disclosure is not limited to the particular methodology, materials, and modifications described and as such may, of course, vary. It is also understood that the terminology used herein is for the purpose of describing particular aspects only, and is not intended to limit the scope of the claims.

Unless defined otherwise, all technical and scientific terms used herein have the same meaning as commonly understood to one of ordinary skill in the art to which this disclosure pertains. It should be understood that any methods, devices, or materials similar or equivalent to those described herein can be used in the practice or testing of the example embodiments. The assembly of the present disclosure could be driven by hydraulics, electronics, and/or pneumatics.

It should be appreciated that the term "substantially" is synonymous with terms such as "nearly," "very nearly," "about," "approximately," "around," "bordering on," "close to," "essentially," "in the neighborhood of," "in the vicinity of," etc., and such terms may be used interchangeably as appearing in the specification and claims. It should be appreciated that the term "proximate" is synonymous with terms such as "nearby," "close," "adjacent," "neighboring," "immediate," "adjoining," etc., and such terms may be used interchangeably as appearing in the specification and claims. The term "approximately" is intended to mean values within ten percent of the specified value.

It should be appreciated that the apex vertebra, apex, or apex of the curve is the vertebra or disk with the greatest rotation or farthest deviation from the center of the vertebral column. End vertebrae are those with the maximal tilt toward the apex of the curve.

It should be appreciated that the term "fluid" is synonymous with the term "material" as pertaining to the substance injected into the inflatable balloon anchor, and such terms may be used interchangeably as appearing in the specification and claims. The fluid (or material) that is injected into the inflatable balloon anchor is, at least during the injection process, generally a substance that has no fixed shape and yields easily to external pressure, for example, a liquid, a gas, a heterogeneous mixture (i.e., a mixture comprising solid particles suspended in a liquid), or an amorphous solid. Following the injection process, the fluid in the inflatable balloon anchor may remain in its original state as, for example, a liquid, or may transform into a solid. A fluid that transforms into a solid is referred to as a "hardenable" fluid (or material). A fluid that absorbs into the body after alignment has been completed is referred to as an absorbable fluid (or material).

Figure 1:
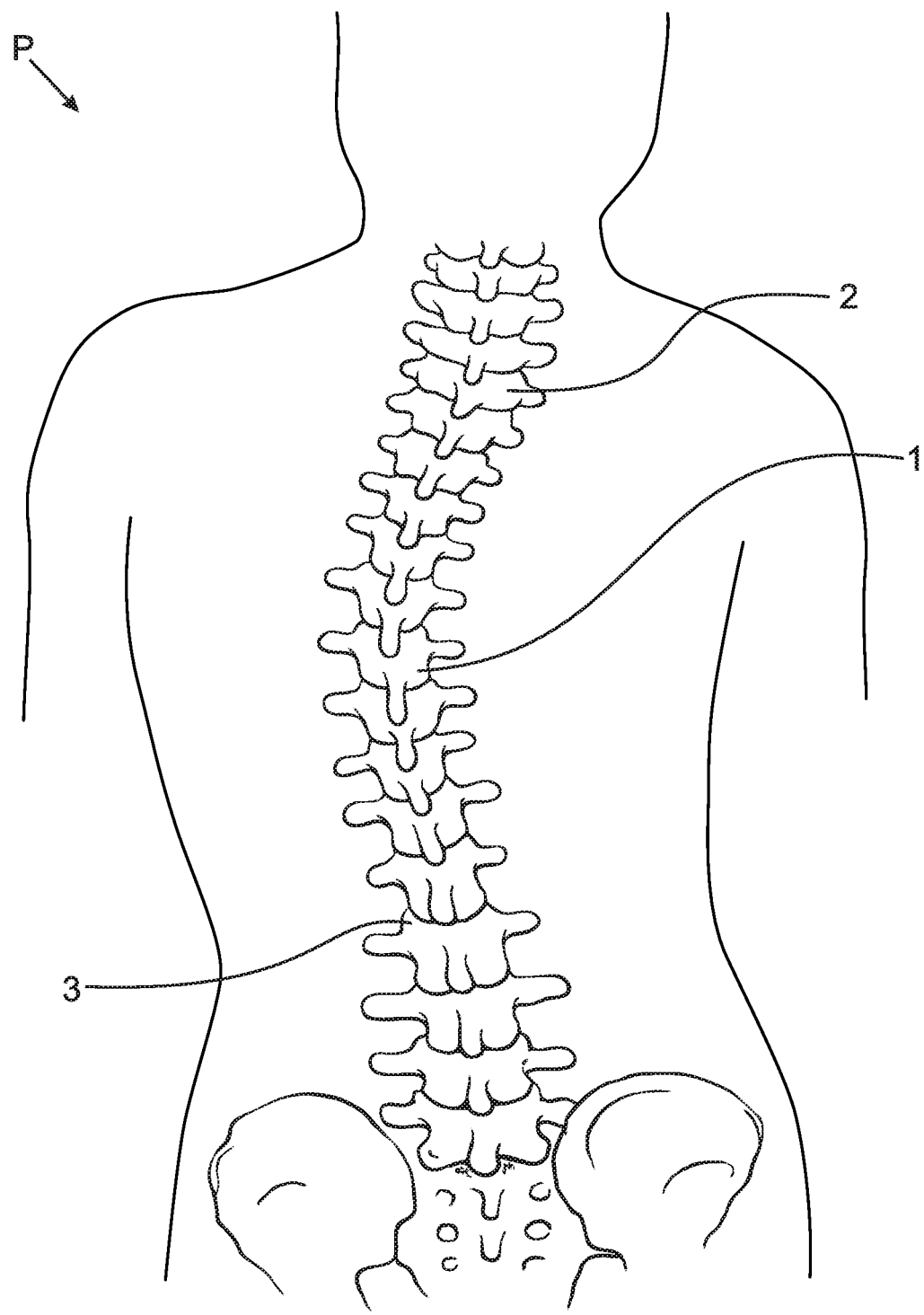
FIG. 1 is a stylized posterior view of a person with a spine afflicted with scoliosis.
Figure 2A:
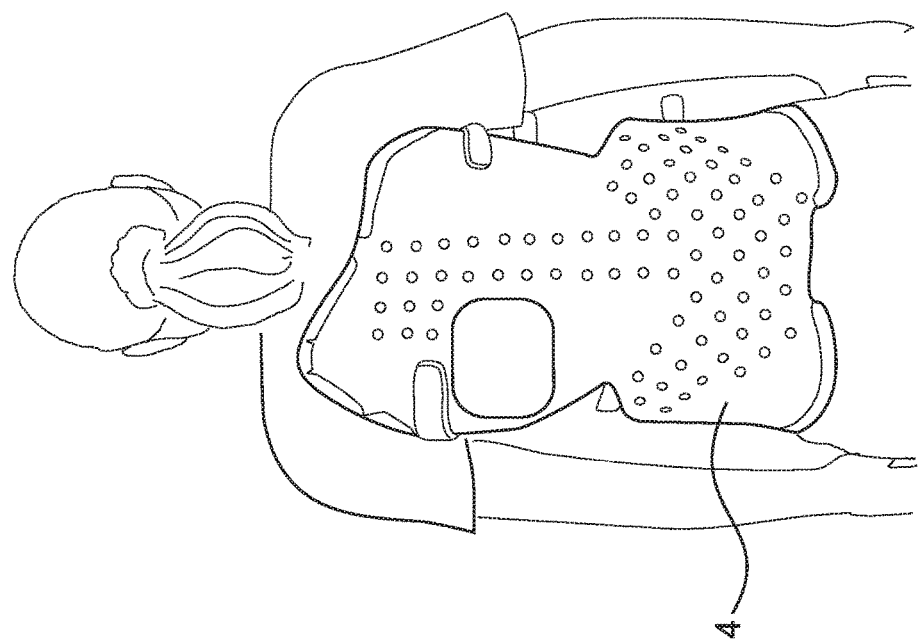
FIG. 2A is a rear view of a person with scoliosis wearing a full body brace as known in the prior art.
Figure 2B:
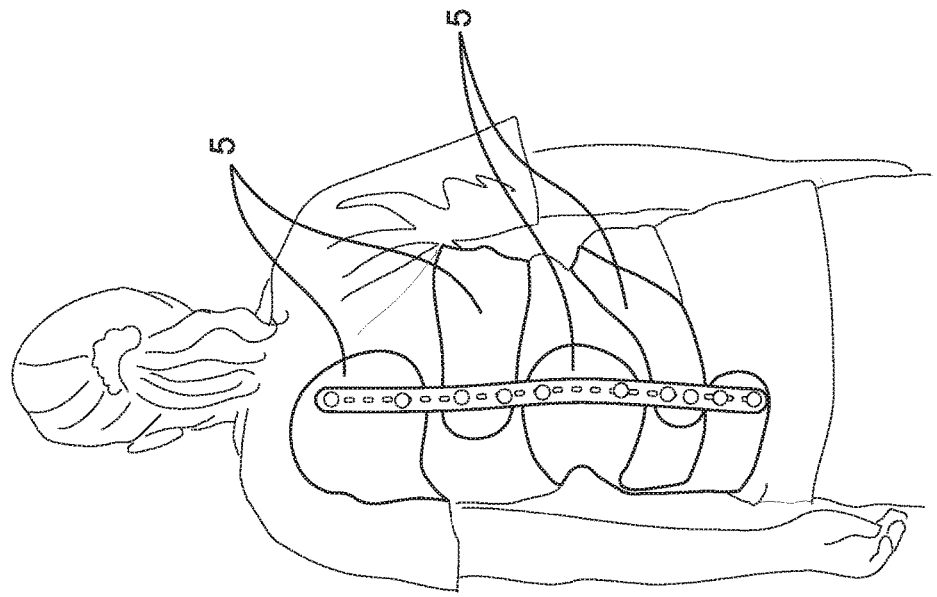
FIG. 2B is a rear view similar to that of FIG. 2A but showing a lighter prior art brace.
Figure 3:
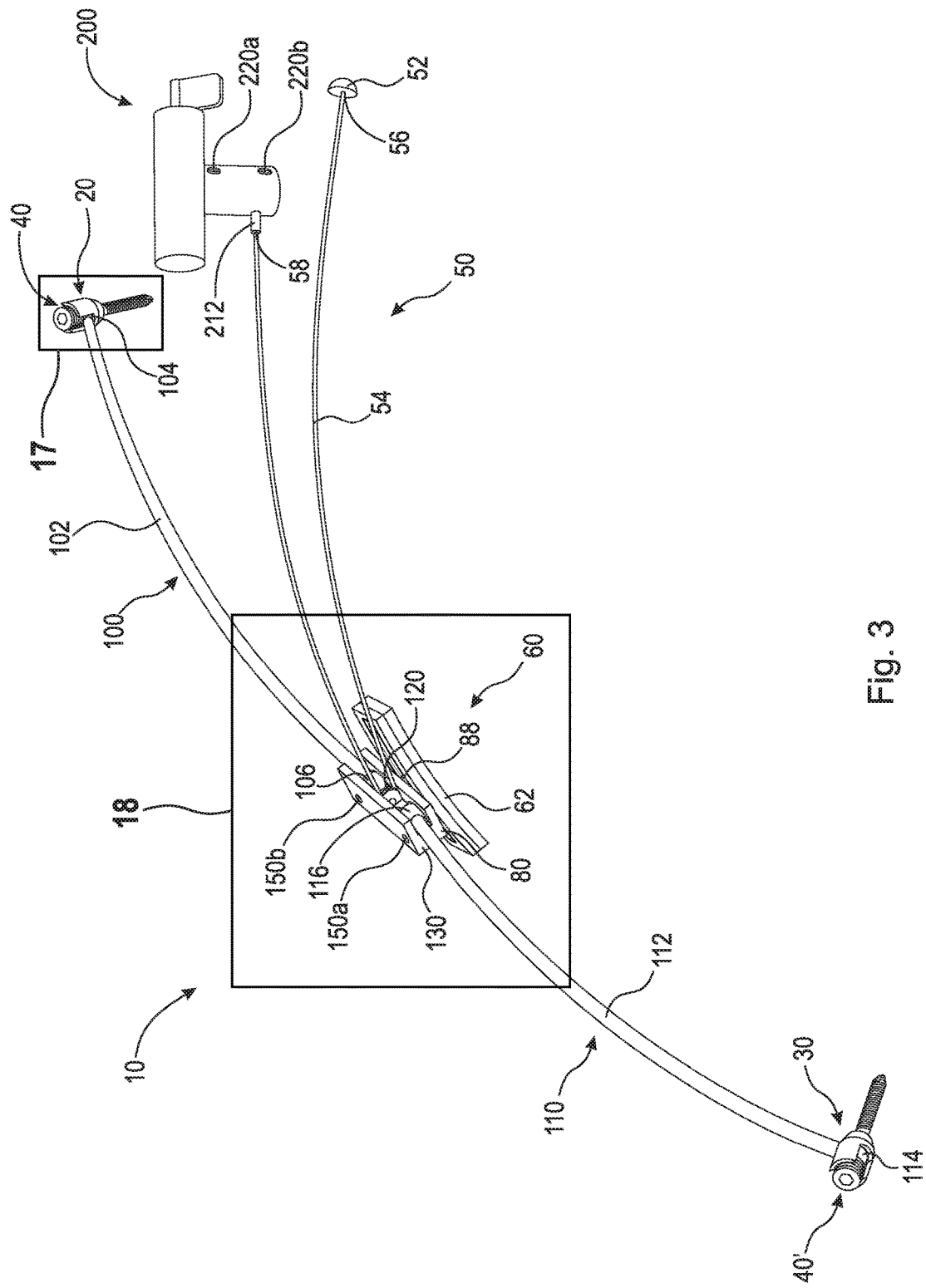
FIG. 3 is a perspective view of a subcutaneous implantable device.
Figure 4:
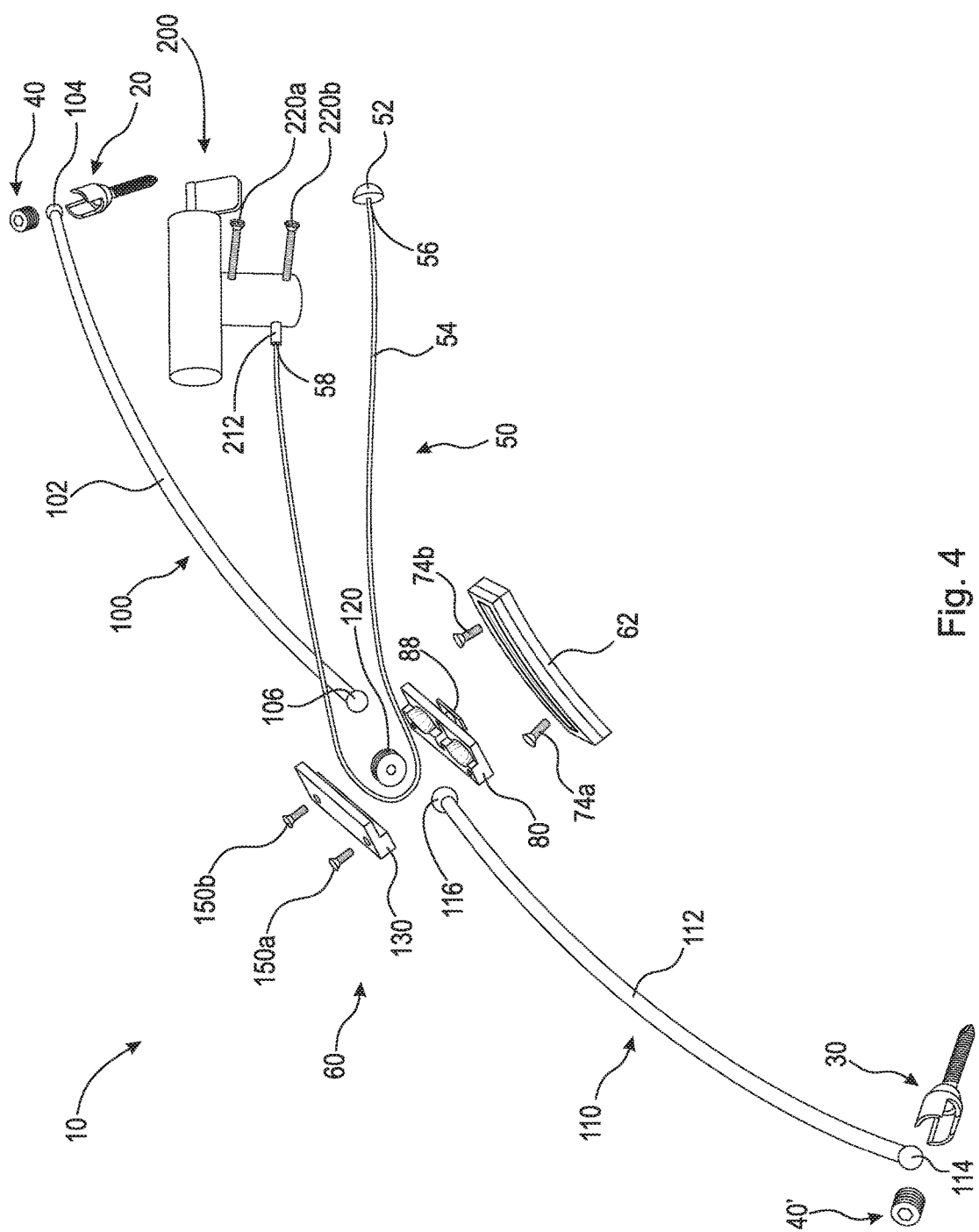
FIG. 4 is a perspective exploded view of the device shown in FIG. 3.

Referring now to the figures, FIG. 3 is a perspective view of a subcutaneous implantable device 10. FIG. 4 is a perspective exploded view of subcutaneous implantable device 10 shown in FIG. 3. Subcutaneous implantable device 10 generally comprises pedicle screw 20, pedicle screw 30, set screw 40, set screw 40', tensioning member 50, stabilizing plate assembly 60, rod 100, rod 110, pulley 120, and winding assembly 200.

Figure 5:
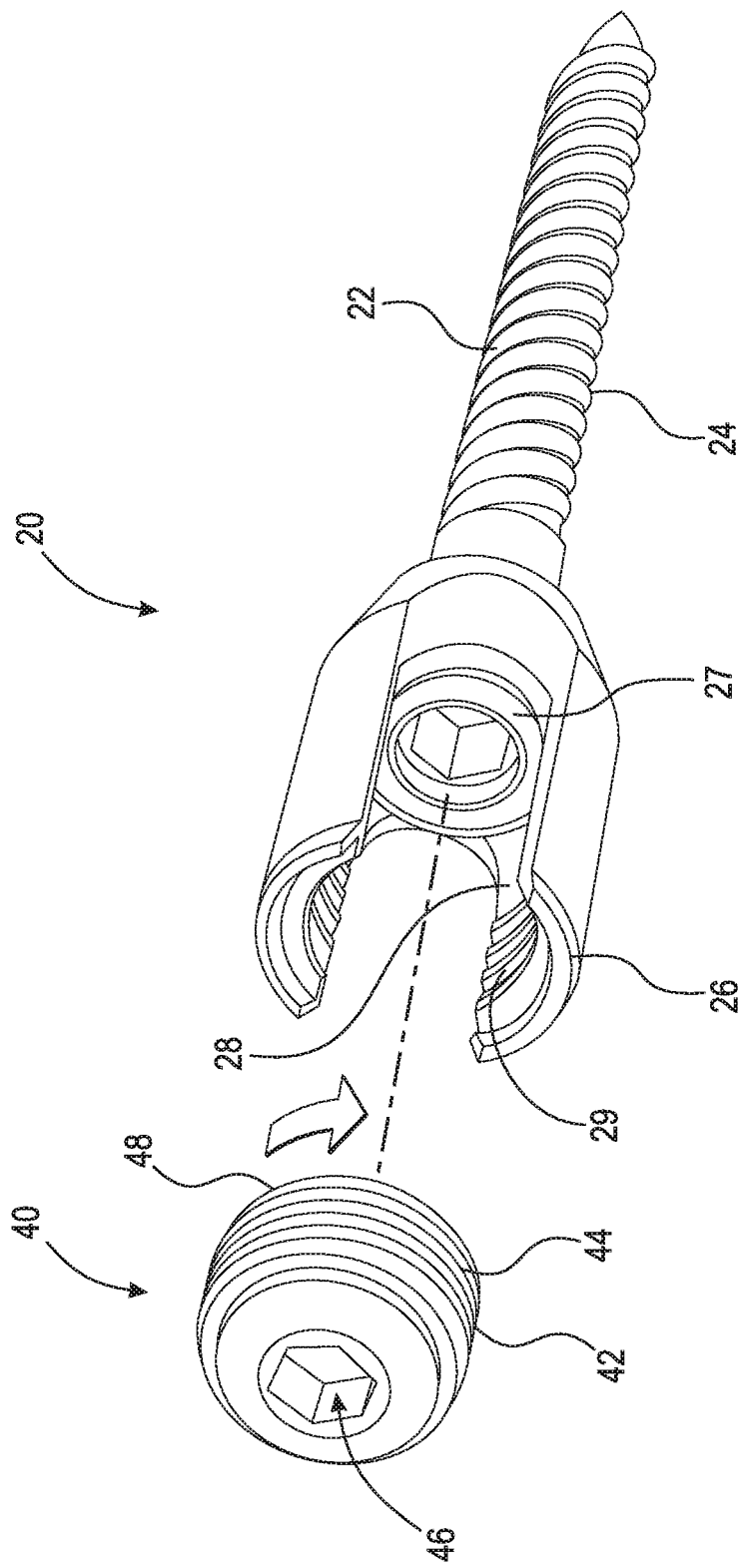
FIG. 5 is a perspective view of a pedicle screw and a set screw of the device shown in FIG. 3.

FIG. 5 is a perspective view of pedicle screw 20 and set screw 40 of subcutaneous implantable device 10 shown in FIG. 3. Pedicle screw 20 comprises screw member 22 and connector member 26. Screw member 22 comprises external threads 24 and is secured into the pedicle of a vertebra at the top of a spinal curvature leaving connector member 26 protruding from the vertebra. Connector member 26 is U-shaped and comprises contact surface 27 and side wall 28. Contact surface 27 is generally spherical in shape and acts as a socket for end ball 104, as will be discussed in greater detail below. Side wall 28 is generally a radially inward facing surface including internal threads 29. The U-shape of connector member 26 allows pedicle screw 20 to be screwed into the pedicle using a tool, such as a hex screwdriver or a flat head screwdriver.

Pedicle screw 30 is substantially identical to pedicle screw 20. Pedicle screw 30 is shown in FIGS. 3 and 4 but is not shown in detail. Pedicle screw 30 comprises screw member 32 and connector member 36. Screw member 32 comprises external threads 34 and is secured into the pedicle of a vertebra at the bottom of a spinal curvature leaving connector member 36 protruding from the vertebra. Connector member 36 is U-shaped and comprises contact surface 37 and side wall 38. Contact surface 37 is generally spherical in shape and acts as a socket for end ball 114 as is discussed in greater detail below. Side wall 38 is generally a radially inward facing surface including internal threads 39. The U-shape of connector member 36 allows pedicle screw 30 to be screwed into the pedicle using a tool, such as a hex screwdriver or flat head screwdriver.

Set screw 40 comprises radially outward facing surface 42, screw head 46, and contact surface 48. Radially outward facing surface 42 comprises external threads 44. Set screw is screwed into pedicle screw 20 and external threads 44 engage internal threads 29. Contact surface 48 is generally spherical in shape and acts as a socket for end ball 104, as will be discussed in greater detail below. Screw head 46 comprises any type of design used to turn set screw 40. In an example embodiment, screw head 46 is a hex socket head that can be driven using a hex key, hex wrench, Allen key, or Allen wrench. Any other suitable screw head type, such as slot, cross, Phillips, Frearson, JIS B 1012, Mortorq, Pozidriv, Supadriv, Robertson (square), double-square, triple-square, double hex socket, Torx, or external hex may be used.

Set screw 40' is substantially identical to set screw 40. Set screw 40' is shown in FIGS. 3 and 4 but is not shown in detail. Set screw 40' comprises radially outward facing surface 42', screw head 46', and contact surface 48'. Radially outward facing surface 42' comprises external threads 44'. Set screw is screwed into pedicle screw 30 and external threads 44' engage internal threads 39. Contact surface 48' is generally spherical in shape and acts as a socket for end ball 114, as will be discussed in greater detail below. Screw head 46' comprises any type of design used to turn set screw 40'. In an example embodiment, screw head 46' is a hex socket head that can be driven using a hex key, hex wrench, Allen key, or Allen wrench. Any other suitable screw head type, such as slot, cross, Phillips, Frearson, JIS B 1012, Mortorq, Pozidriv, Supadriv, Robertson (square), double-square, triple-square, double hex socket, Torx, or external hex may be used.

Rod 100 comprises shaft 102, end ball 104, and end ball 106. End ball 104 is pivotably secured to pedicle screw 20 by set screw 40. End ball 104 is inserted into connector member 26 within sidewall 28. Set screw 40 is screwed into connector member 28 such that end ball 104 is firmly secured between contact surface 48 and contact surface 27. The spherical curvature of contact surfaces 48 and 27, when end ball 104 is secured therebetween, creates a ball and socket type connection allowing shaft 102 to pivot about end ball 104. End ball 106 is secured in a similar fashion in stabilizing plate assembly 60, as will be discussed in greater detail below.

Rod 110 comprises shaft 112, end ball 114, and end ball 116. End ball 114 is pivotably secured to pedicle screw 30 by set screw 40'. End ball 114 is inserted into connector member 36 within sidewall 38. Set screw 40' is screwed into connector member 36 such that end ball 114 is firmly secured between contact surface 48' and contact surface 37. The spherical curvature of contact surfaces 48' and 37, when end ball 114 is secured therebetween, creates a ball and socket type connection allowing shaft 112 to pivot about end ball 114. End ball 116 is secured in a similar fashion in stabilizing plate assembly 60, as will be discussed in greater detail below. In an example embodiment, rod 110 is substantially identical (i.e., length, shaft diameter, ball diameter, elasticity, etc.) to rod 100. However, it should be appreciated that rod 110 can have any dimensions and properties suitable for gradually aligning the spine. For example, rod 110 might be shorter or longer than rod 100, depending on which rib stabilizing plate assembly 60 is secured to.

In an example embodiment, one or more extension sleeves can be used to adjust the length of rod 100 and/or rod 110 during the surgical procedure (not shown). In this embodiment, rod 100 would not comprise end ball 104 and rod 110 would not comprise end ball 114. Instead, the extension sleeves would comprise an end ball at one end, which would be secured in the corresponding pedicle screw. At the other end, the extension sleeve would be connected to the end of the rod and secured thereto using any suitable means (e.g., a set screw, threading on the rod/extension sleeve, etc.). The purpose of the extension sleeves is to provide a quick sturdy way to adjust the length of the rods during surgery. For example, the surgeon can have a plurality of extension sleeves of various lengths and can choose the appropriate length extension sleeve during the operation.

Tensioning member 50 comprises inflatable balloon anchor 52 and line 54. Line 54 is a hollow tube and comprises end 56 and end 58. Inflatable balloon anchor 52 is attached to line 54 at end 56. Fluids may be introduced into inflatable balloon anchor 52 through line 54. In an example embodiment, line 54 is a cylindrical cord connected to inflatable anchor 52 at end 56 and a separate hollow tube is attached to a port in inflatable balloon anchor 52. In such embodiment, fluids may be introduced into inflatable balloon anchor 52 through the separate hollow tube. In an example embodiment, line 54 is a solid tube that is hollow proximate end 56, wherein fluids may be introduced into inflatable balloon anchor 52 at the hollow portion. Preferably, line 54 and inflatable balloon anchor 52 are fabricated from polyglycolic acid or other similar biologically compatible absorbable material, which can withstand the tensile force created on line 54 and the strain created on inflatable balloon anchor 52, as described below, and absorb into the body well after the alignment procedure is completed. It should be appreciated that line 54 and inflatable balloon anchor 52 may be fabricated from biologically compatible non-absorbable materials. Inflatable balloon anchor 52 is secured to the apex vertebra as discussed in greater detail below. Line 54 wraps around pulley 120 and end 58 is secured to winding assembly 200. Winding assembly 200 is adjusted to create tension in line 54, which in turn pulls winding assembly 200 and the apex vertebra towards stabilization plate assembly 60, thereby straightening the spine. Winding assembly 200 is discussed in greater detail below. Inflatable balloon anchor 52 may also include array 53. Array 53 is a solid portion of inflatable balloon anchor 52 that abuts against the apex vertebra once inflatable balloon anchor 52 is inflated. This is shown in greater detail in FIGS. 15C-D and 16C-D. Inflatable balloon anchor 52 can be injected with a hardenable fluid such as polymethyl methacrylate (PMMA) or type of cement, an absorbable fluid such as bone putty, or any other material suitable to withstand the tensile force or strain created on inflatable balloon anchor 52.

Figure 6:
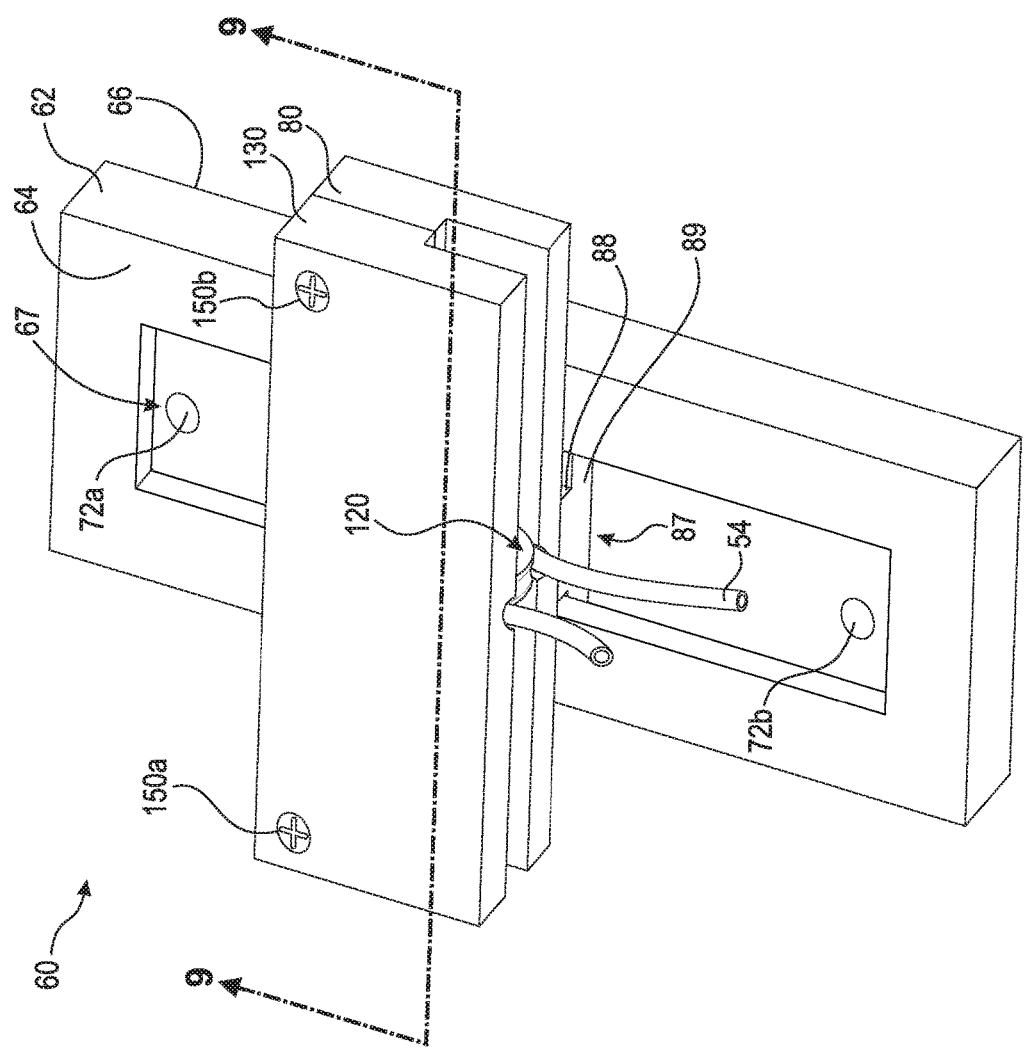
FIG. 6 is a front top perspective view of a stabilizing plate assembly including a lower component, an upper component, a pulley, and a locking plate.
Figure 7A:
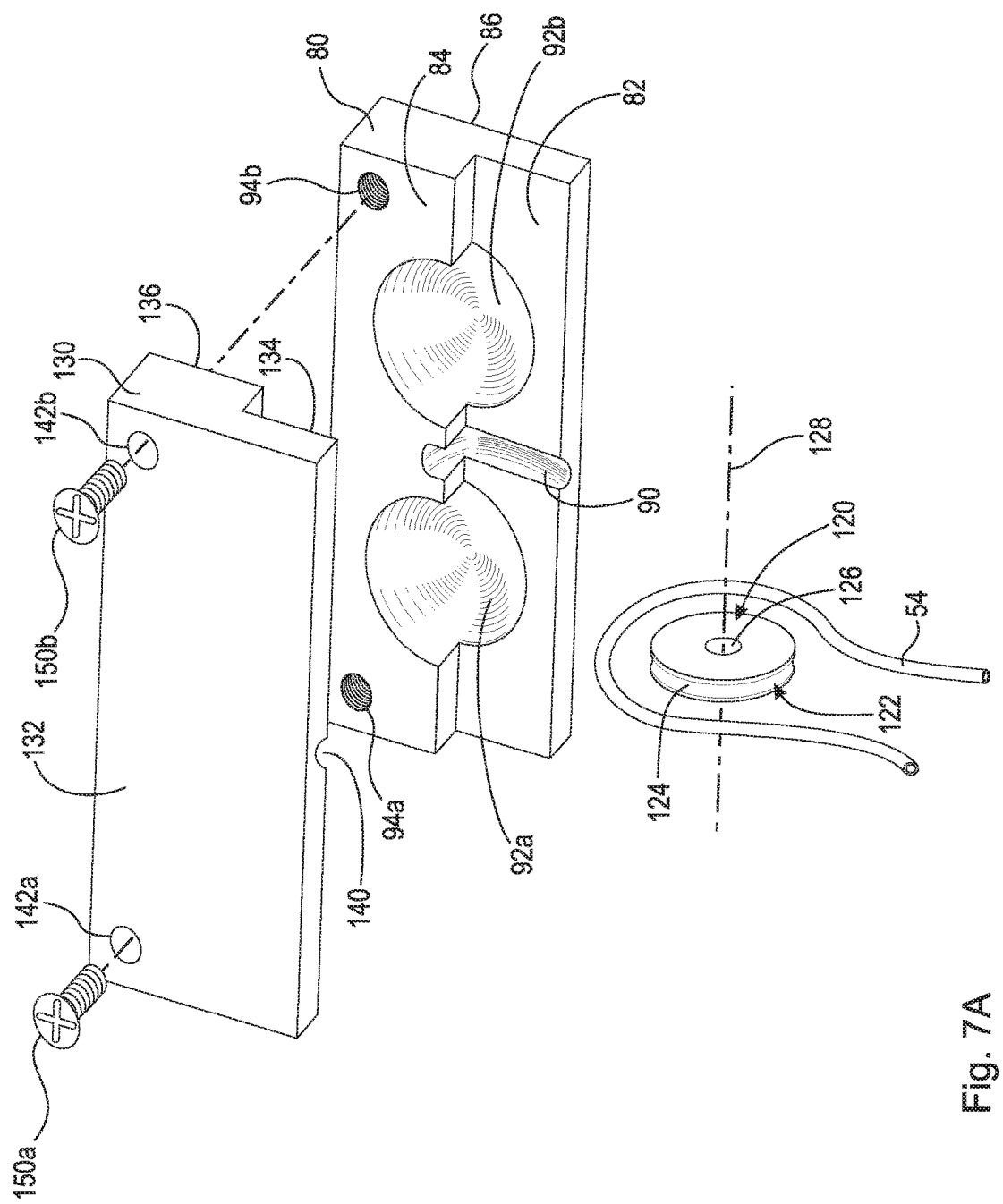
FIG. 7A is a top perspective exploded view of the partial stabilizing plate assembly shown in FIG. 6.
Figure 7B:
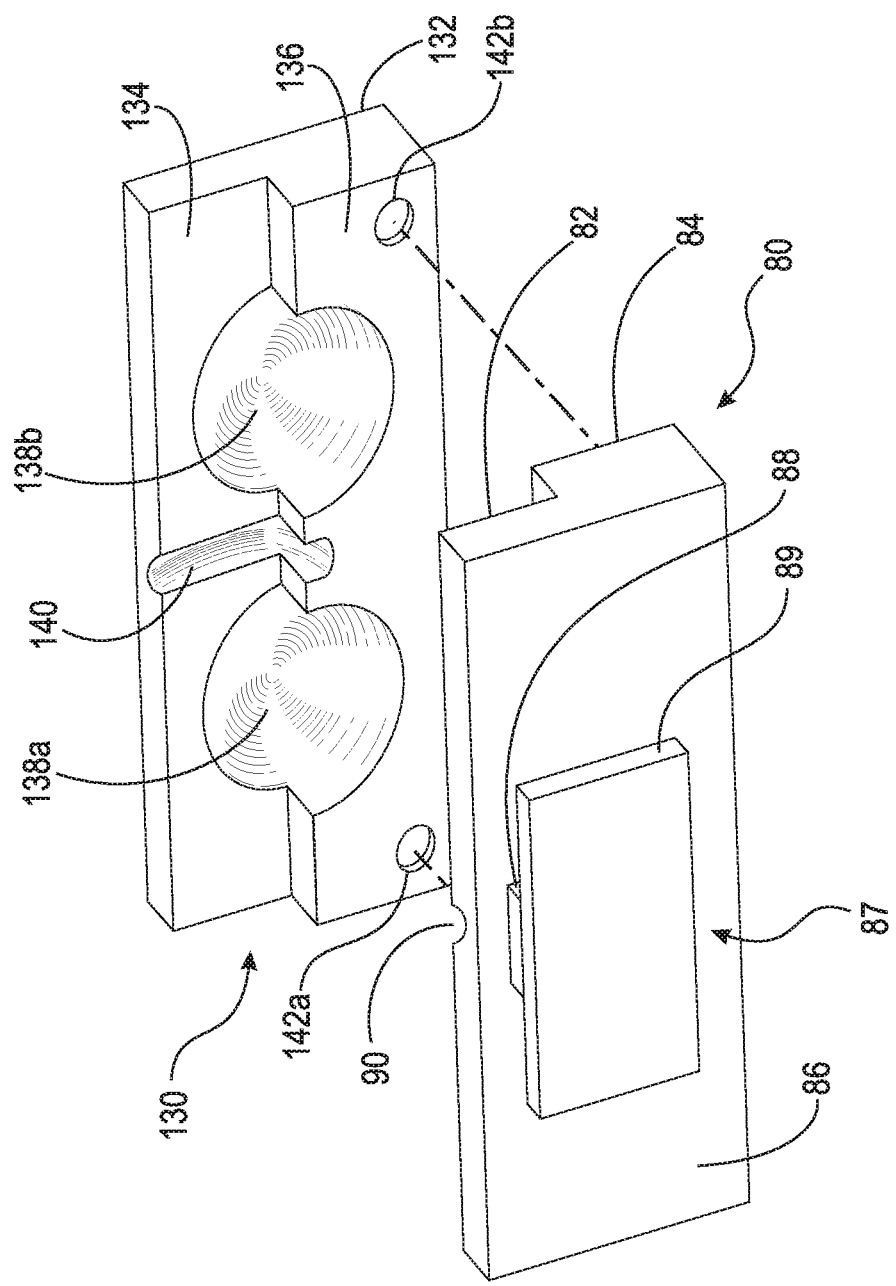
FIG. 7B is a bottom perspective exploded view of the partial stabilizing plate assembly shown in FIG. 6.

FIG. 6 is a front top perspective view of stabilizing plate assembly 60. FIG. 7B is a top perspective exploded view of stabilizing plate assembly 60 shown in FIG. 6. FIG. 7B is a bottom perspective exploded view of stabilizing plate assembly 60 shown in FIG. 6. Stabilizing plate assembly 60 generally comprises lower component 62, upper component 80, pulley 120, and locking plate 130.

Upper component 80 comprises first top surface 82, second top surface 84, bottom surface 86, and runner 87 (shown in FIG. 7B). First top surface 82, second top surface 84, and bottom surface 86 are substantially planar surfaces. Sockets 92a and 92b are arranged on first and second top surfaces 82 and 84, as shown in the figures. Socket 92a is generally a spherical surface and acts as a contact surface or socket for end ball 106 as is discussed in greater detail below. Socket 94b is generally a spherical surface and acts as a contact surface or socket for end ball 116 as is discussed in greater detail below. First top surface 82 comprises groove 90. Groove 90 is a radial cutout in first top surface 82 arranged to secure pulley 120. Runner 87 is a nob that protrudes from bottom surface 86. Runner 87 comprises shaft 88 and flange 89. Flange 89 is arranged in channel 68 of track 67 described infra. As described in greater detail below, sides 69a and 69b enclose flange 89 within channel 68 while shaft 88 extends through opening 70. In an example embodiment, second top surface 84 further comprises threaded holes 94a and 94b for connecting locking plate 130 to upper component 80. However, it should be appreciated that any other suitable method of connecting locking plate 130 to upper component 80, such as clamps or adhesive, may be used.

Locking plate 130 comprises top surface 132, first bottom surface 134, and second bottom surface 136. Top surface 132 and first and second bottom surfaces 134 and 136 are substantially planar surfaces. Sockets 138a and 138b are arranged on first and second bottom surfaces 134 and 136, as shown in the figures. Socket 138a is generally a spherical surface and acts as a contact surface or socket for end ball 106 as is discussed in greater detail below. Socket 138b is generally a spherical surface and acts as a contact surface or socket for end ball 116 as is discussed in greater detail below. First bottom surface 134 comprises groove 140. Groove 140 is a radial cutout in first bottom surface 134 arranged to secure pulley 120. In an example embodiment, locking plate 130 further comprises through-bores 142a and 142b. Screws 150a and 150b are inserted through through-bores 142a and 142b and screwed into threaded holes 94a and 94b, respectively, to secure locking plate 130 to upper component 80.

Pulley 120 comprises radially outward facing surface 122. Radially outward facing surface 122 comprises groove 124 arranged to completely house line 54 therein. For example, when line 54 is wrapped around the secured pulley 120, line 54 is completely arranged radially inward from radially outward facing surface 122 such that line 54 does not contact upper component 80 or locking plate 130. In an example embodiment, pulley 120 is rotatingly secured between lower component 62 and locking plate 130. Specifically, pulley 120 at least partially engages grooves 90 and 140 and is rotatingly fixed substantially about axis of rotation 128. Friction between line 54 and groove 124 causes pulley 120 to rotate substantially about axis of rotation 128. In an example embodiment, pulley 120 is non-rotatably secured between upper component 80 and locking plate 130. In this embodiment, groove 124 has a low coefficient of friction and line 54 easily slides around pulley 120. For example, line 54 is made of titanium having a Teflon® coating and easily slides around groove 124. In an example embodiment, pulley 120 further comprises radially inward facing surface 126. In this embodiment, pulley 120 can be rotatably secured to an axle about axis of rotation 128. In an example embodiment, pulley 120 is arranged between upper component 80 and locking plate 130 such that pulley 120 can swivel therein.

Figure 9:
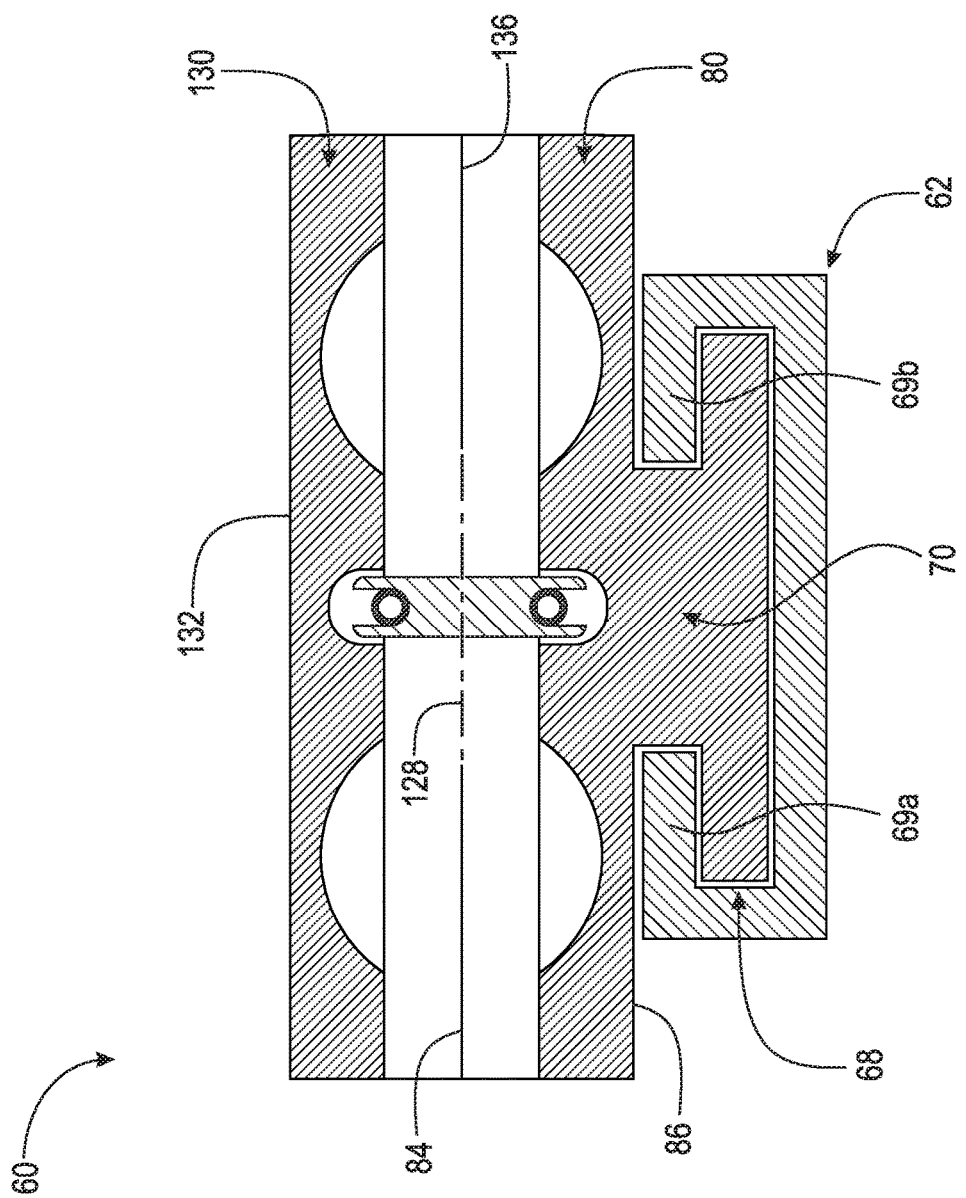
FIG. 9 is a cross-sectional view taken generally along line 9-9 in FIG. 6.

FIG. 8 is a top perspective view of lower component 62 shown in FIG. 6. FIG. 9 is a cross-sectional view taken generally along line 9-9 in FIG. 6. Lower component 62 comprises top surface 64, bottom surface 66, and track 67. Lower component 62 is fixed to a patient's rib such that bottom surface 66 abuts against the rib. Lower component 62 can be fixed to the rib with screws, clamps, or any other suitable method. In an example embodiment, lower component 62 comprises through-bores 72a and 72b and is secured to a rib via screws 74a and 74b (see FIG. 4). Through-bores 72a and 72b are preferably arranged in track 67 and are countersunk such that when screws 74a and 74b are secured, they do not hinder movement of upper component 80 within track 67. As shown in FIG. 9, track 67 generally comprises channel 68, sides 69a and 69b, and opening 70. Track 67 is designed to enclose runner 87 while still allowing upper component 80 to slidingly connect to lower component 62. Upper component 80 is arranged to engage lower component 62 such that upper component 80 can slide and at least partially rotate with respect to lower component 62 without disengaging from lower component 62. An assembly of this type is known by those having ordinary skill in the art. In an example embodiment, upper component 80 is arranged to slide but not rotate with respect to lower component 62.

Figure 10:
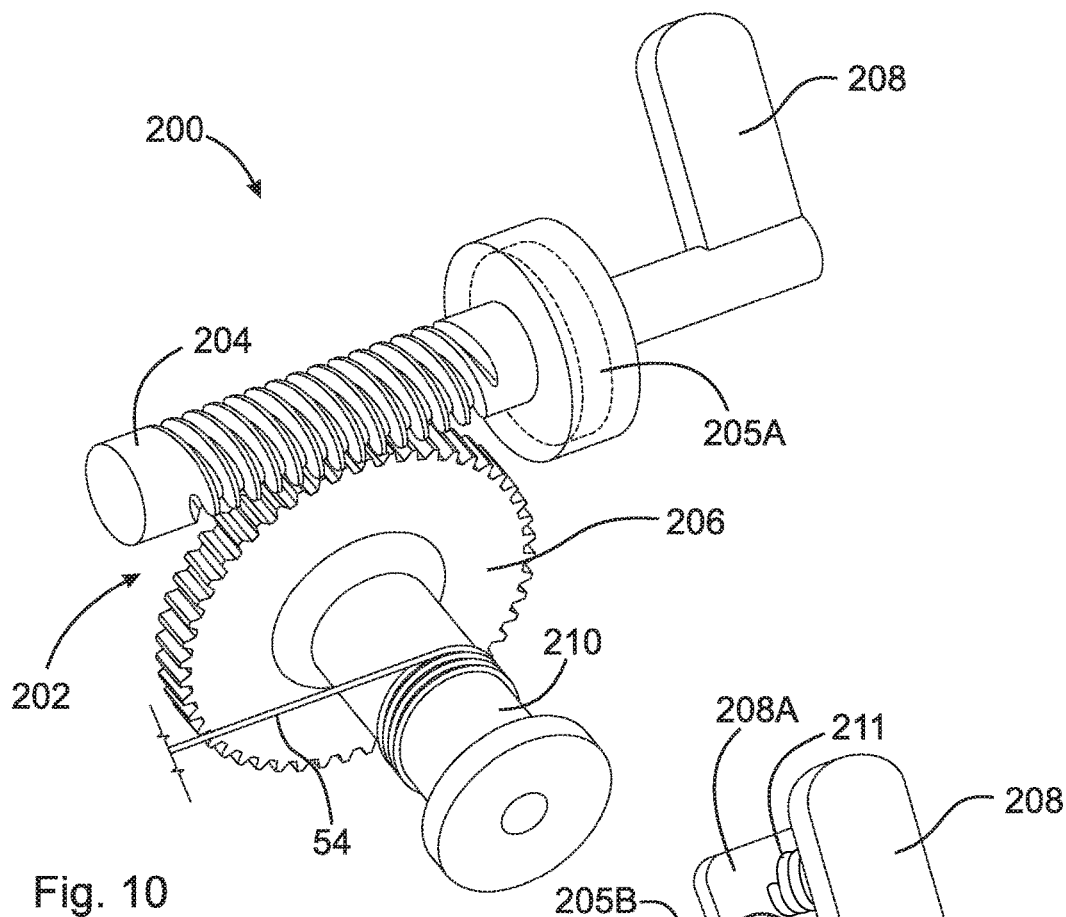
FIG. 10 is a top perspective view of a winding assembly for performing a gradual lateral spinal alignment of a spine.

FIG. 10 is a top perspective view of winding assembly 200 for performing a gradual lateral spinal alignment of a spine. In the configuration shown, the winding means is in the form of ratcheting mechanism 202, for example, a worm gear, which includes screw 204 that interacts with wheel 206. It should be appreciated that screw 204 could be a worm screw and that wheel 206 could be a worm wheel. Wheel 206 includes stem 210, which holds or retains line 54. Control lever 208 acts as a control means and is operatively attached to screw 204 to turn screw 204 a predetermined amount when pressed. By "operatively attached" it is meant that a component or device is connected either directly or indirectly to a second component and causes that second component to function, e.g., turn a predetermined amount. As can be seen in FIG. 10, when screw 204 turns, wheel 206 also rotates which in turn rotates stem 210 to wind line 54. It should be appreciated that due to the frictional relationship between screw 204 and wheel 206, wheel 206 cannot rotate screw 204. Spring 205A is provided to enable control lever 208 to rebound to its starting position so that control lever 208 can only be moved a predetermined amount when pressed. Spring 205A is in the form of a torsion spring, for example. It should be appreciated that wheel 206, and thus stem 210, is activated by activating the actuator. In the embodiment shown in FIGS. 10 and 11, the actuator, control lever 208, is actuated by applying a physical force to control lever 208 through the skin (i.e., a doctor or medical professional can activate control lever 208 and tighten line 54). In an example embodiment, control lever 208 may be actuated by repetitive digital compression transcutaneously.

Figure 11:
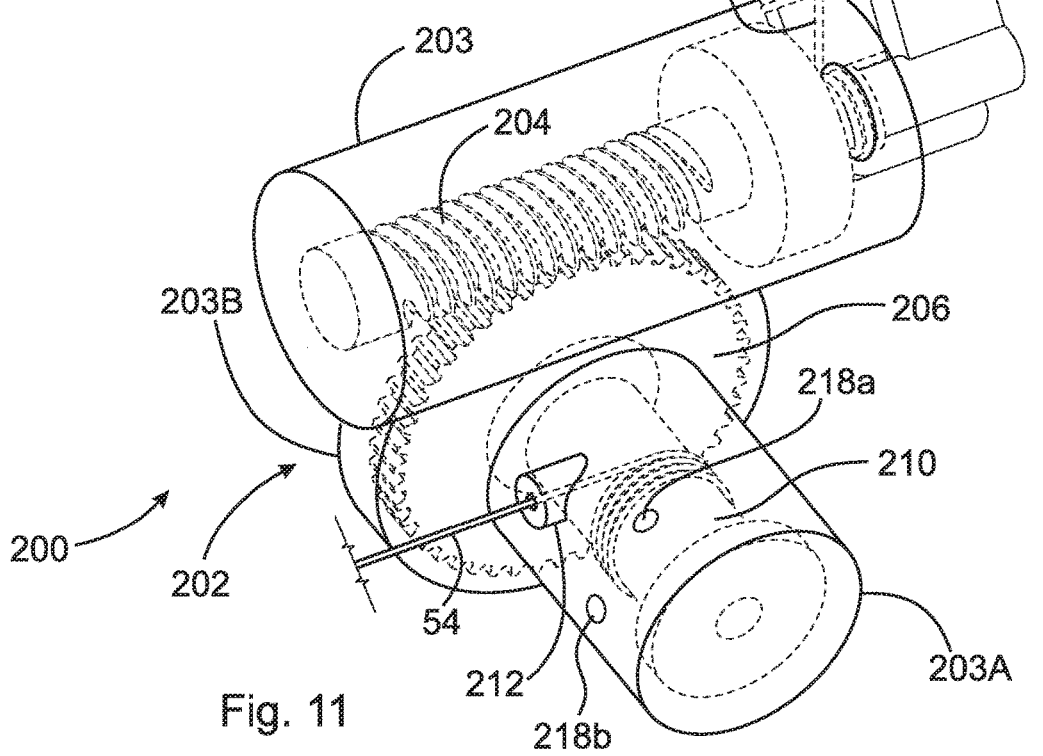
FIG. 11 is a top perspective view of the winding assembly shown in FIG. 10 enclosed in a housing.

FIG. 11 is a top perspective view of winding assembly 200 shown in FIG. 10 enclosed in a housing. FIG. 11 is a top perspective view of ratcheting mechanism 202 enclosed in housing 203. It is apparent to those having skill in the art that housing 203 may be a single unit enclosing ratcheting mechanism 202 or may include separately elements that enclose the individual components of ratcheting mechanism 202, such as housing 203A, enclosing stem 210 as seen in FIG. 11. It should be appreciated that housing 203 can be made of any suitable casing for example, a silicone elastomer. Preferably, spring 205B is included to enable control lever 208 to rebound to its starting position creating a ratchet effect so that control lever 208 can only be moved a predetermined amount when pressed. Spring 205B can be in the form of a coil spring attached to housing 203 in which control lever 208 is caused to return to a starting position. Control lever 208 may rebound to a starting position off coil spring 211 attached to rebound board 208A. Persons having ordinary skill in the art recognize that although FIGS. 10-11 depict different spring means that act to return control lever 208 to a starting position, preferably, only one spring means is utilized in any one particular ratcheting mechanism 202.

Figure 12A:
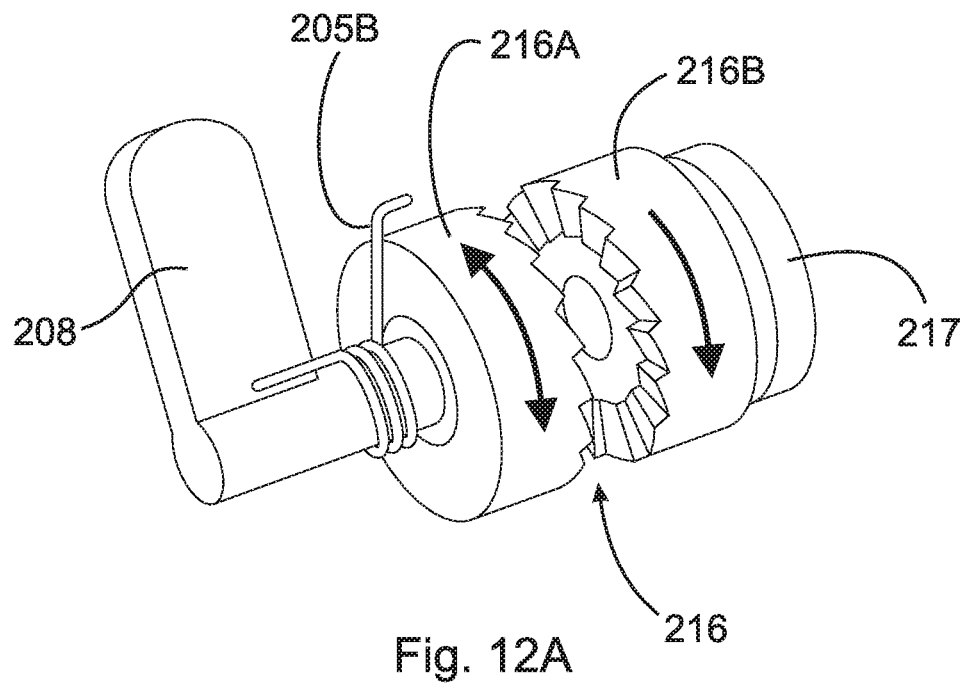
FIG. 12A is a top perspective view of a ratchet assembly used in an example embodiment of a winding assembly for performing gradual spinal alignments.
Figure 12B:
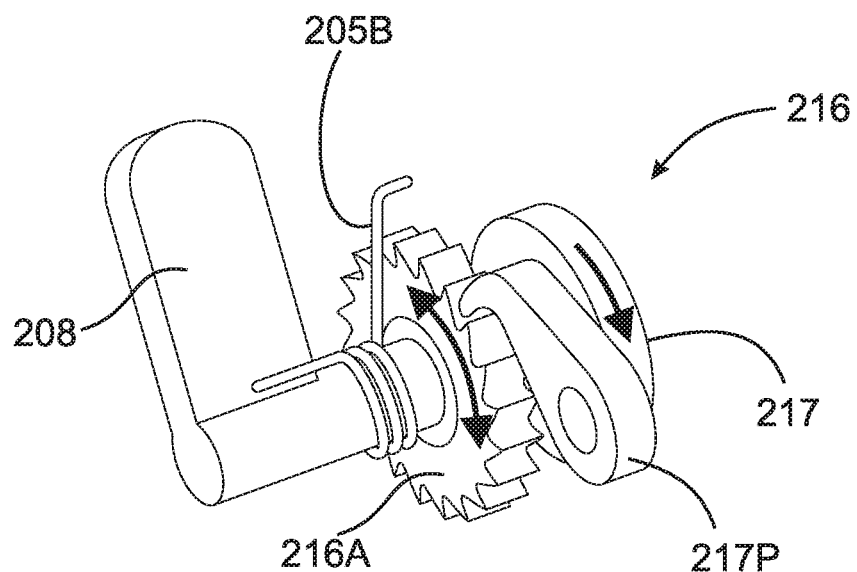
FIG. 12B is a top perspective view of a ratchet assembly used in an example embodiment of a winding assembly for performing gradual spinal alignments.

FIG. 12A is a top perspective view of ratchet assembly 216 used in an example embodiment of winding assembly 200 for performing gradual spinal alignments. FIG. 12B is a top perspective view of ratchet assembly 216 used in an example embodiment of winding assembly 200 for performing gradual spinal alignments. The winding means may be a ratchet mechanism used to control the rotation of stem 210 through ratcheting mechanism 202, or directly through control of ratchet assembly 216 as shown in FIGS. 12A and 12B. In FIG. 12A, control lever 208 is operatively attached to ratchet gear 216A, which engages ratchet gear 216B to rotate ratchet gear 216B in a single direction. In FIG. 12B, control lever 208 is operatively attached to a single ratchet gear 216A and control lever 208 can rotate ratchet gear 216A in a single direction via pawl 217P. Pawl 217P is connected to housing 203 surrounding ratchet assembly 216 (shown in FIG. 11). Spring 217 acts to maintain rotational tension in ratchet assembly 216 to return control lever 208 to its starting position. Persons having ordinary skill in the art recognize that a worm screw, such as screw 204, may be attached to ratchet assembly 216 to enable ratcheting mechanism 202 to be rotated a predetermined amount and thus pull line 54 a predetermined amount with each press of control lever 208.

Figure 13:
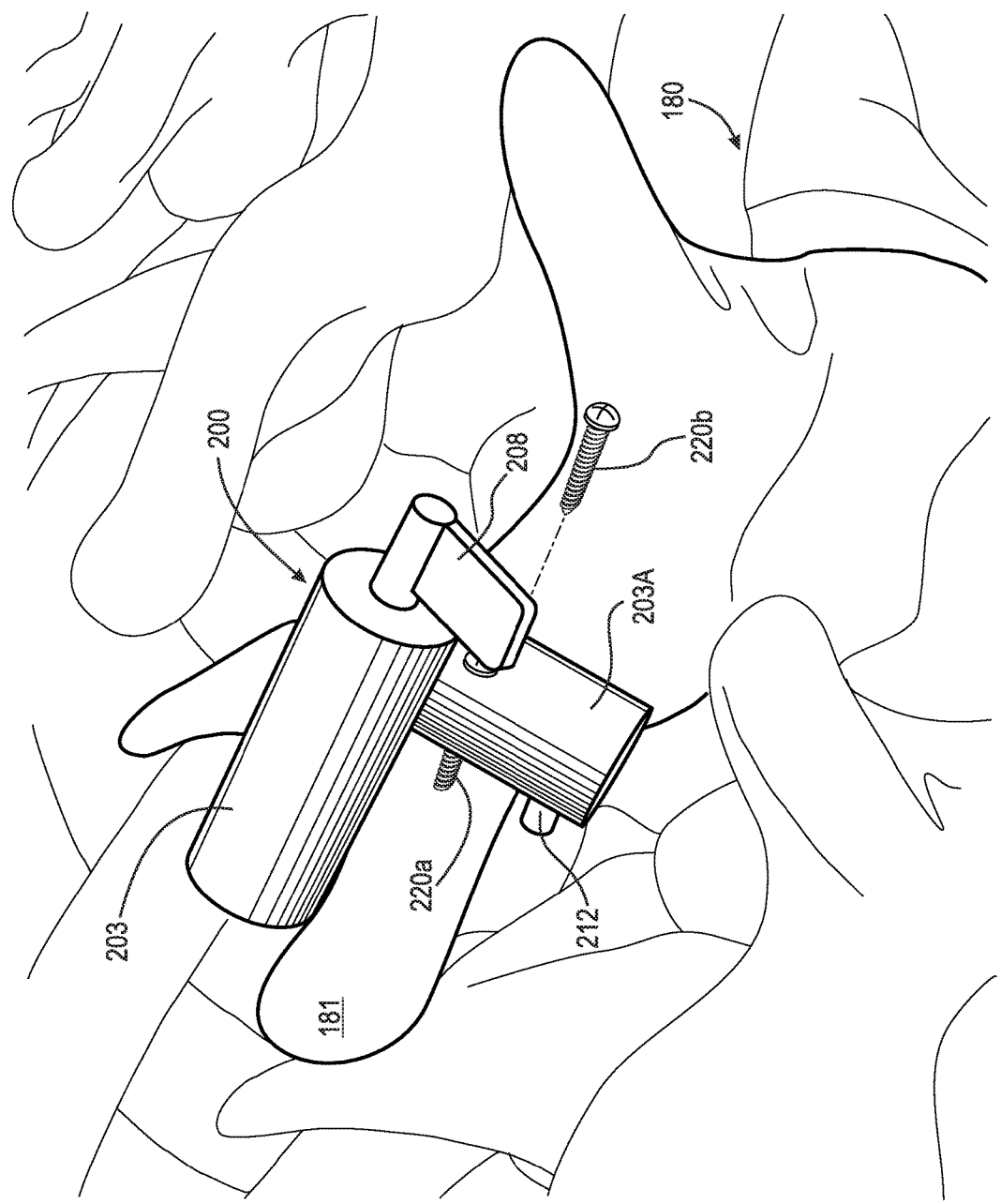
FIG. 13 is a perspective view of the winding assembly shown in FIG. 11 secured to a vertebra of a spinal column with screws.

FIG. 13 is a perspective view of winding assembly 200 shown in FIG. 11, secured to a vertebra of a spinal column with screws 220a and 220b. Specifically, winding assembly 200 is secured to spinous process 181 of vertebra 180. Winding assembly 200 is secured to the spinous process of the apex vertebra. In an example embodiment, winding assembly 200 is secured to the spinous process of a vertebra adjacent to the apex vertebra. The components of ratcheting mechanism 202 are enclosed in housings 203, 203A, and 203B. FIG. 13 also includes a posterior schematic view of a spinal column comprising vertebrae and intervertebral disks. In an example embodiment, ratcheting mechanism 202 is secured to one of vertebrae via screws 220a and 220b. Screws 220a and 220b pass through through-bores 218a and 218b of housing 203A, respectively, and secure into the vertebra. Preferably, ratcheting mechanism 202 is attached in such a way as to allow control lever 208 to be proximate to the external side of surrounding tissue to enable it to be operated, e.g., pressed, from outside the body of a patient. Although not shown in FIG. 13, preferably, a spring means such as those discussed above, is included in winding assembly 200 to ensure line 54 is wound only a predetermined amount when control lever 208 is pressed, once identified by palpation through the skin. In this exemplary embodiment, control lever 208 can be activated subcutaneously to create force on line 54.

In an example embodiment, winding assembly 200 comprises an actuator portion that can be actuated to create tension in line 54. For example, winding assembly 200 can include an actuator portion having a magnet that allows tension to be put on line 54 by use of an External Remote Controller. In another example, winding assembly 200 includes an actuator or a motor that can be energized with radio frequency or ultrasonic energy. It should be appreciated that any suitable means of continuously creating tension in line 54 may be used.

Figure 13A:
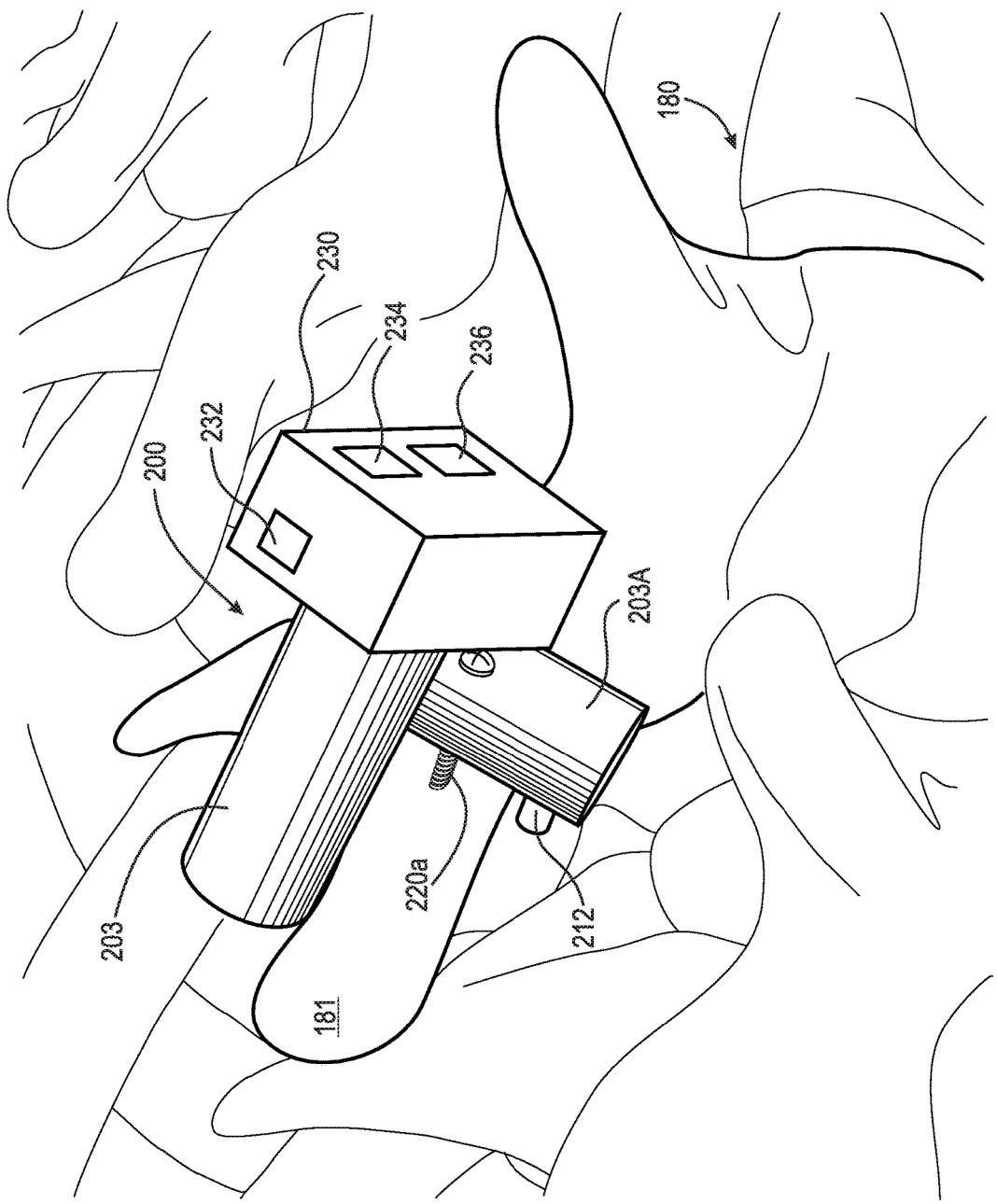
FIG. 13A is an example embodiment showing a motor as an actuator portion.

FIG. 13A is an example embodiment showing motor 230 as an actuator portion that creates tension in line 54. In this example embodiment, motor 230 that drives wheel 206, and thus stem 210. Motor 230 includes wireless receiver 232 that, when a signal is sent to receiver 232, activates motor 230. In this example embodiment, motor 230 can be actuated by wireless communications such as radio frequency transmission (i.e., radio waves), optical wireless communication (i.e., light), ultrasound communication (i.e., sending signals using ultrasonic waves), other electromagnetic wireless technologies, such as magnetic or electric fields, or any other suitable signal known to those of ordinary skill in the art. In this example embodiment, motor 230 may be an ultrasonic motor, a piezoelectric motor, or an ultrasonic piezoelectric motor, as is known to those of ordinary skill in the art. Receiver 232 may be an ultrasound transducer, specifically a receiver or transceiver, capable of converting ultrasound into electric signals. Motor 230 may also include power source 234. Power source 234 may be, for example, a battery. Intra thecal pumps and spinal cord stimulators are already in use and are powered by implantable batteries as are pacemakers. In an example embodiment, motor 230 may be powered externally by radio frequency or ultrasound energy, as is known in the art. Piezoelectric motors are favored for their high power to weight ratio, their high torque, their reliability and lack of need for maintenance, their controllability to a nanometer level, their silence, their lack of need for a gear box, and, more recently, their improved cost. Piezoelectric motors are increasingly being used in robotics and could easily be used to power subcutaneous implantable device 10, and create tension in line 54, with or without a worm drive gearing mechanism. In an example embodiment, multiple short rods are implanted at different locations along the spine at a curvature, each with its own anchor and cable and operated by a micro motor. Motor 230 may also include programmable computer 236. Programmable computer is implanted with motor 230 such that the rate of tensioning in line 54 could be preprogrammed days or weeks at a time.

Figure 14A:
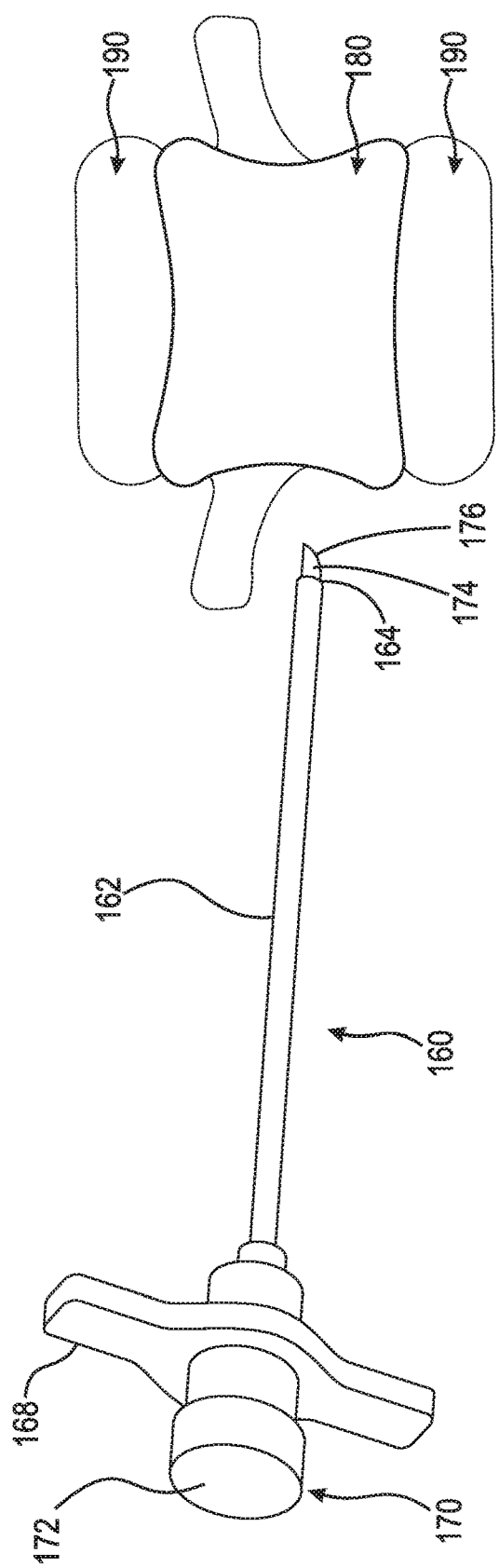
FIG. 14A is a perspective view of a penetrating bone needle with a removable stylet that can be used to attach a tensioning member to an apex vertebra.

FIG. 14A is a perspective view of penetrating bone needle 160 with removable stylet 170 that can be used to attach tensioning member 50 to an apex vertebra. Penetrating bone needle 160 comprises handle 168 and cylindrical needle 162 including ends 164 and 166 (shown in FIG. 14B). Cylindrical needle 162 extends through handle 168. Removable stylet 170 comprises cap 172 and cylindrical needle 174 including tapered cutting tip 176. Cylindrical needle 174 is connected to cap 172 and extends through cylindrical needle 162. When removable stylet 170 is connected to penetrating bone needle 160, cylindrical needle 174 extends past cylindrical needle 162 such that tapered cutting tip 176 is exposed. Tapered cutting tip 176 is used to drill/create a hole in the apex vertebra. For example, penetrating bone needle 160 with removable stylet 170 connected therein is tapped across the apex vertebra to create a hole therethrough. Specifically, the hole is created from the lateral side of the apex vertebra to the contralateral side of the apex vertebra such that cylindrical needle 162 extends past the contralateral side, as will be discussed in greater detail below. Penetrating bone needle 160 may be, for example, a Jamshidi™ needle. It should be appreciated that any other cutting needle suitable for penetrating a vertebra such that inflatable balloon anchor 52 can be inserted may be used as described in this disclosure.

Figure 14B:
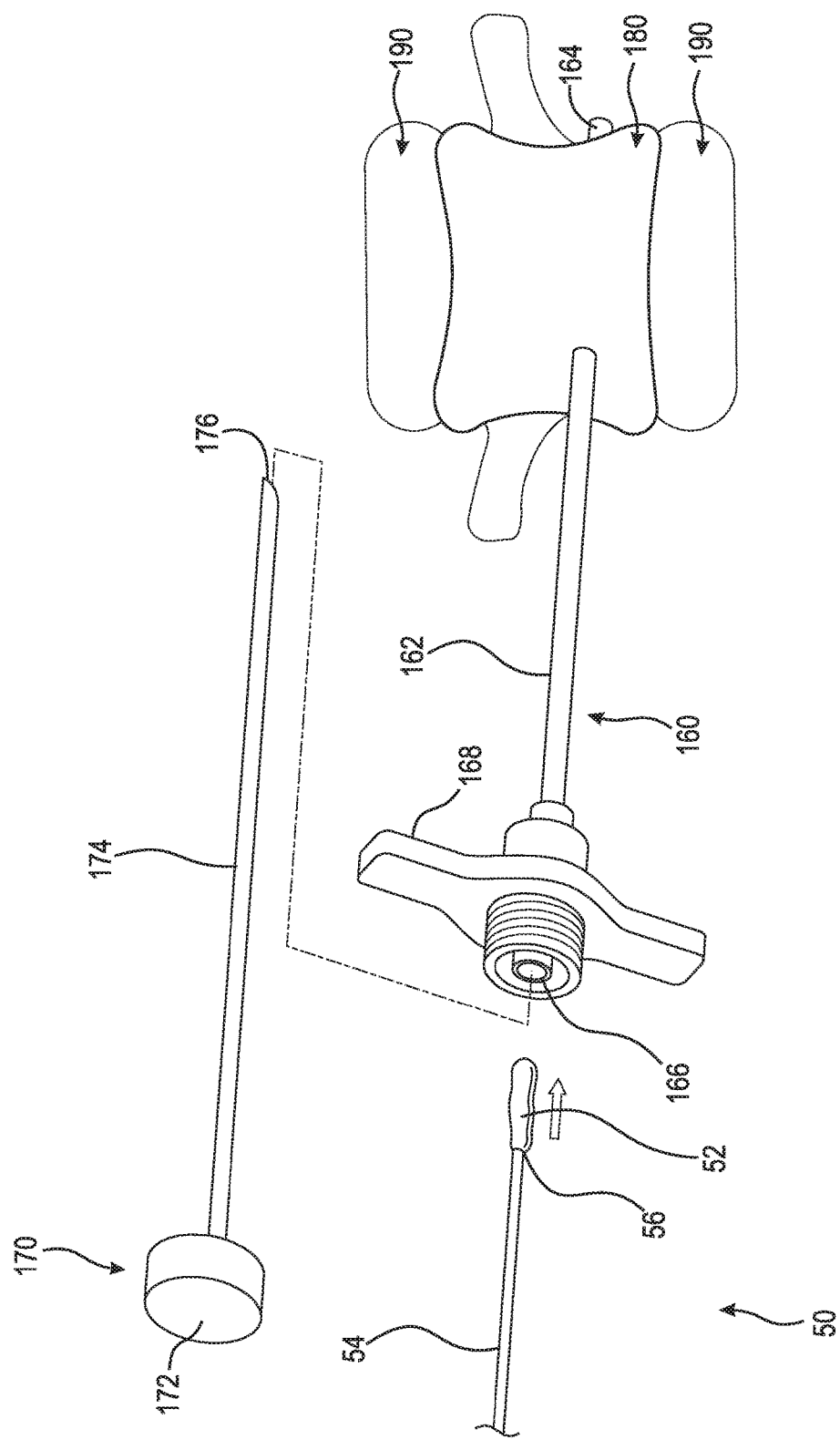
FIG. 14B is a perspective view of the penetrating bone needle shown in FIG. 14A inserted through the apex vertebra. The removable stylet is removed from the penetrating bone needle so that a tensioning member can be inserted therein.

FIG. 14B is a perspective view of penetrating bone needle 160 shown in FIG. 14A inserted through apex vertebra 180. Removable stylet 170 is removed from penetrating bone needle 160 so that tensioning member 50 can be inserted therein. Cap 172 is unscrewed from handle 168 and removable stylet 170, including cylindrical needle 174, is removed from penetrating bone needle 160 exposing end 166. Tensioning member 50 is inserted into end 166 and guided through cylindrical needle 162 toward end 164, as will be discussed in greater detail below.

Figure 15A:
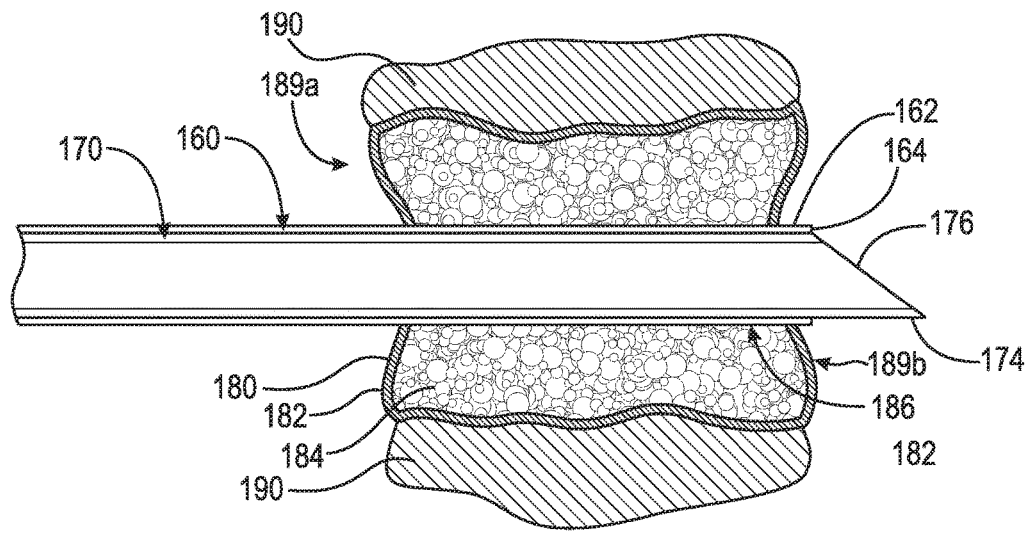
FIG. 15A is a cross-sectional view of a penetrating bone needle inserted through an apex vertebra to create a hole extending from a lateral side to an contralateral side of the apex vertebra.
Figure 15B:
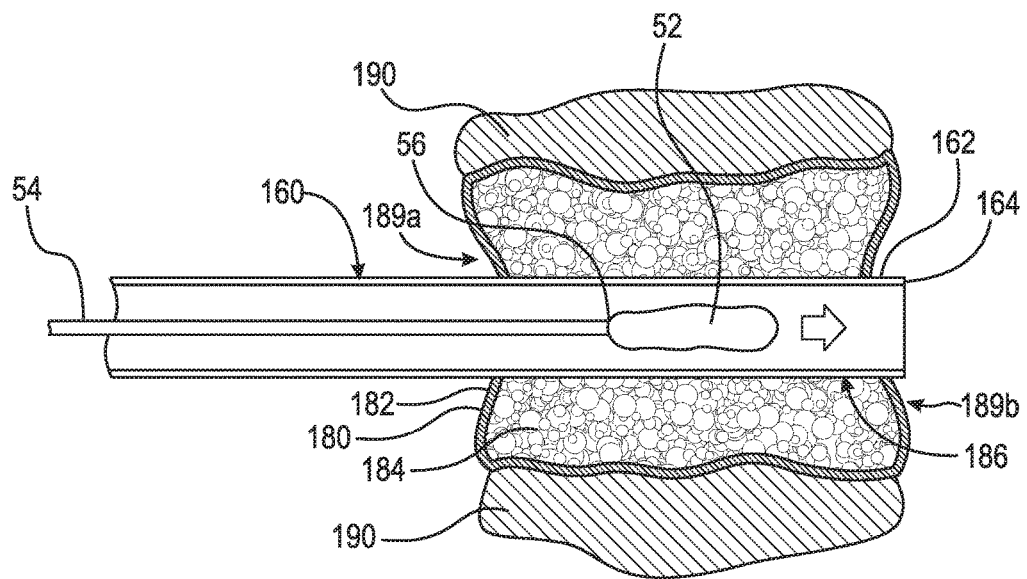
FIG. 15B shows the removable stylet withdrawn from the apex vertebra and a line and an inflatable balloon anchor inserted in the penetrating bone needle from the lateral side of the apex vertebra.
Figure 15C:
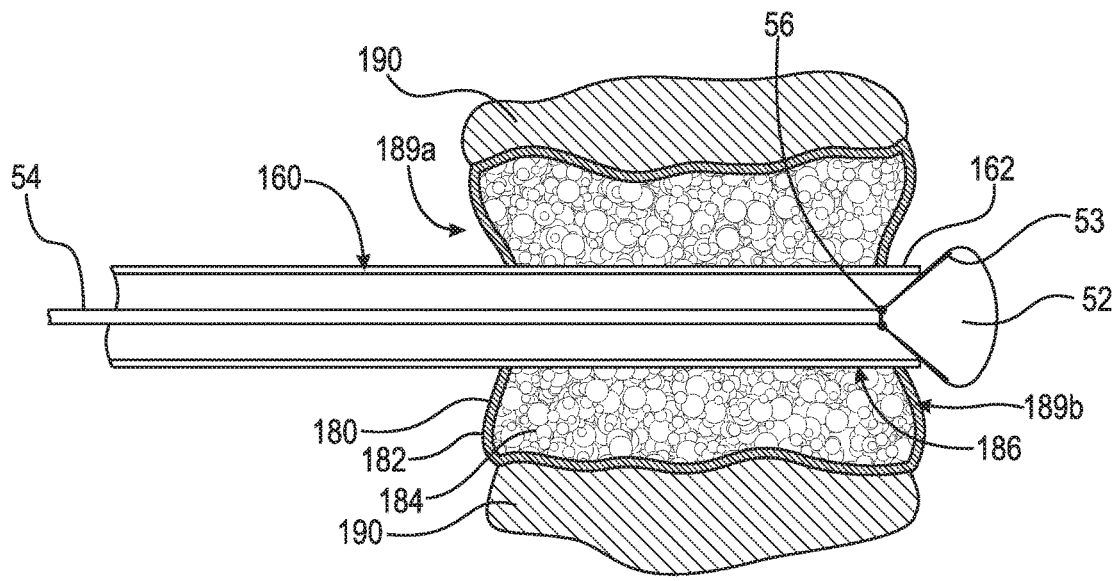
FIG. 15C shows the inflatable balloon anchor partially inflated and positioned on the contralateral side of the apex vertebra and starting to inflate.
Figure 15D:
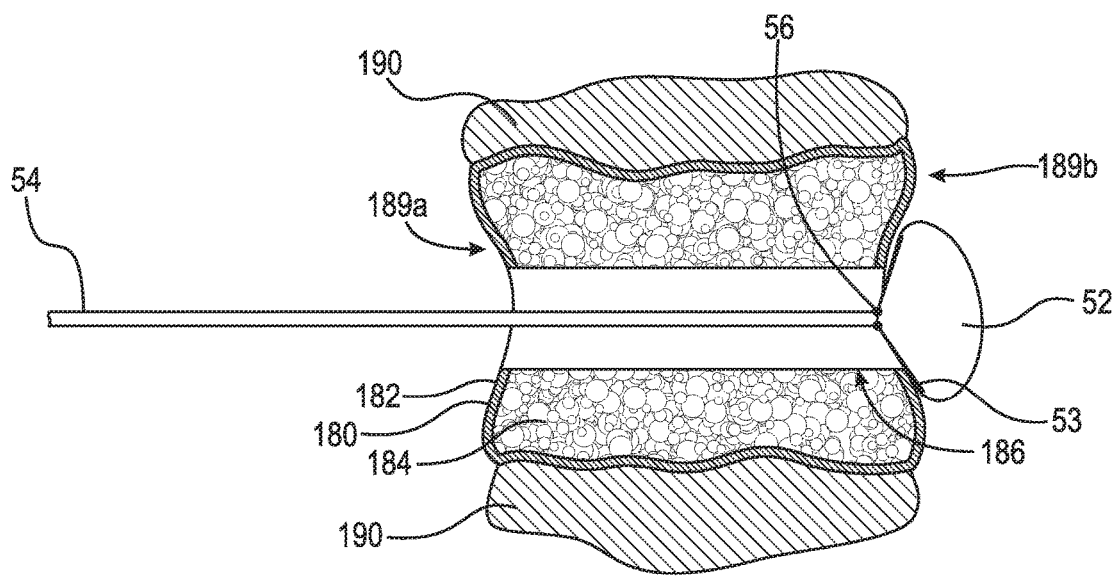
FIG. 15D depicts the inflatable balloon anchor sufficiently inflated and drawn against the contralateral side of the apex vertebra by a line.

FIG. 15A is a cross-sectional view of penetrating bone needle 160 inserted through apex vertebra 180 to create hole 186 extending from lateral side 189a to contralateral side 189b of apex vertebra 180. Hole 186 is formed by tapered cutting tip 176. At the same time, cylindrical needle 162 is guided through hole 186 until end 164 extends past contralateral side 189b, as shown in FIG. 15A. FIG. 15A depicts a first method of attaching inflatable balloon anchor 52 to apex vertebra 180. FIG. 15B shows removable stylet 170 withdrawn from apex vertebra 180 and line 54 and inflatable balloon anchor 52 inserted in cylindrical needle 162 from end 166 (i.e., from lateral side 189a). FIG. 15C shows inflatable balloon anchor 52 positioned on contralateral side 189b of apex vertebra 180 and starting to inflate. Fluid is introduced into inflatable balloon anchor 52 through line 54. As fluid volume increases, inflatable balloon anchor 52 increases in size. FIG. 15D depicts inflatable balloon anchor 52 sufficiently inflated and drawn against contralateral side 189b of apex vertebra 180 by line 54. Penetrating bone needle 160 has been withdrawn from apex vertebra 180, specifically, cylindrical needle 162 is removed from hole 186. Inflatable balloon anchor 52 is sufficiently inflated when its general diameter is larger than the diameter of hole 186. As such, when line 54 is drawn inflatable balloon anchor 52 interferes with cortical material 82 on contralateral side 189b of apex vertebra 180. For temporary anchor fixation, water or saline may be used to inflate inflatable balloon anchor 52. Permanent fixation may be achieved with hardenable fluids such as bone cement, methyl methylacrylate (MMA), polymethyl methacrylate (PMMA), or any other suitable material as is known to those having ordinary skill in the art. An absorbable material such as bone putty may also be used. It should be appreciated that inflatable balloon anchor 52 may be a noncompliant or compliant balloon.

In an example embodiment, inflatable balloon anchor 52 comprises array 53. Array 53 comprises a plurality of arms or vanes operatively attached to the inner surface of inflatable balloon anchor 52 and pivotally attached to line 54. By operatively attached is meant that a component or device is connected either directly or indirectly to a second component and causes that second component to function. For example, each of the plurality of arms in array 53 is operatively attached to the inner surface of inflatable balloon anchor 52 and causes inflatable balloon anchor 52 to open. When line 54 is pulled, the arms of array 53 each open causing inflatable balloon anchor 52 to inflate. Alternatively, when inflatable balloon anchor 52 is inflated, the arms pivotally deploy. Array 53 may be used to open inflatable balloon anchor 52 when greater pulling or traction forces are necessary during the aligning process as explained below.

Figure 16A:
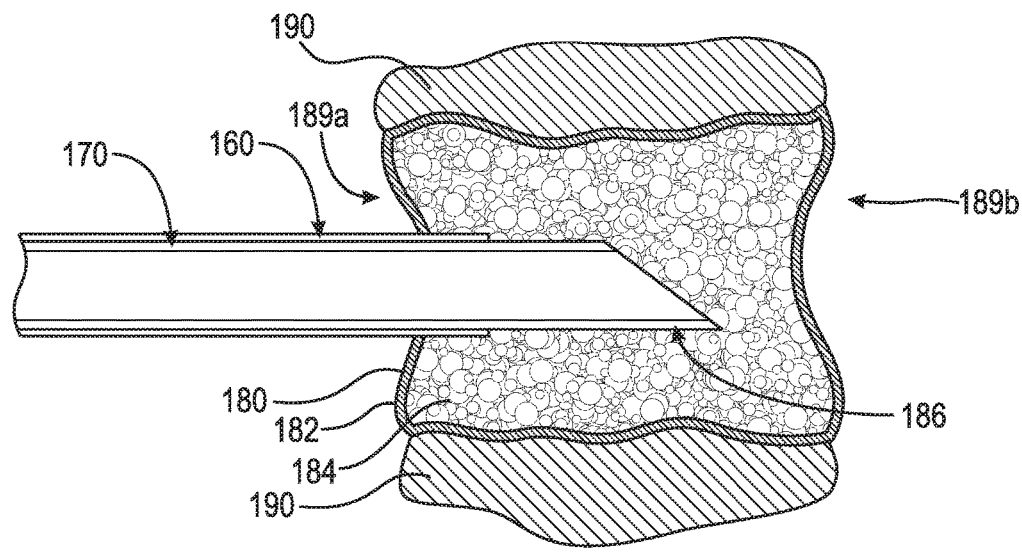
FIG. 16A is a cross-sectional view of a penetrating bone needle, including a removable stylet, a line, and an inflatable balloon anchor therein, inserted into an apex vertebra to create a hole extending from a lateral side of the apex vertebra.
Figure 16B:
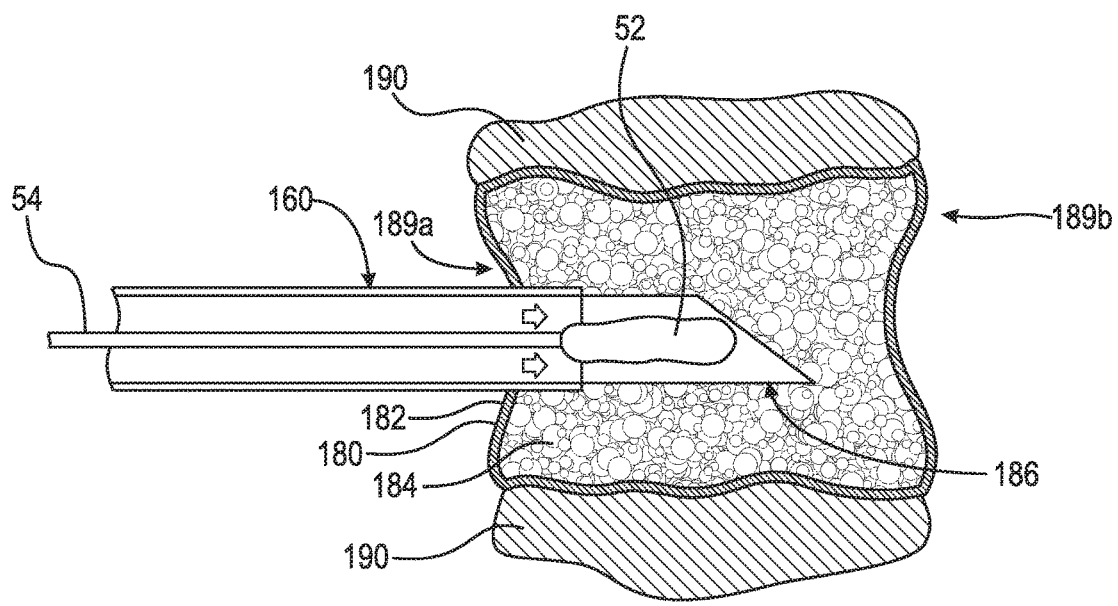
FIG. 16B shows the removable stylet withdrawn from the apex vertebra and the line and the inflatable balloon anchor arranged in the penetrating bone needle.
Figure 16C:
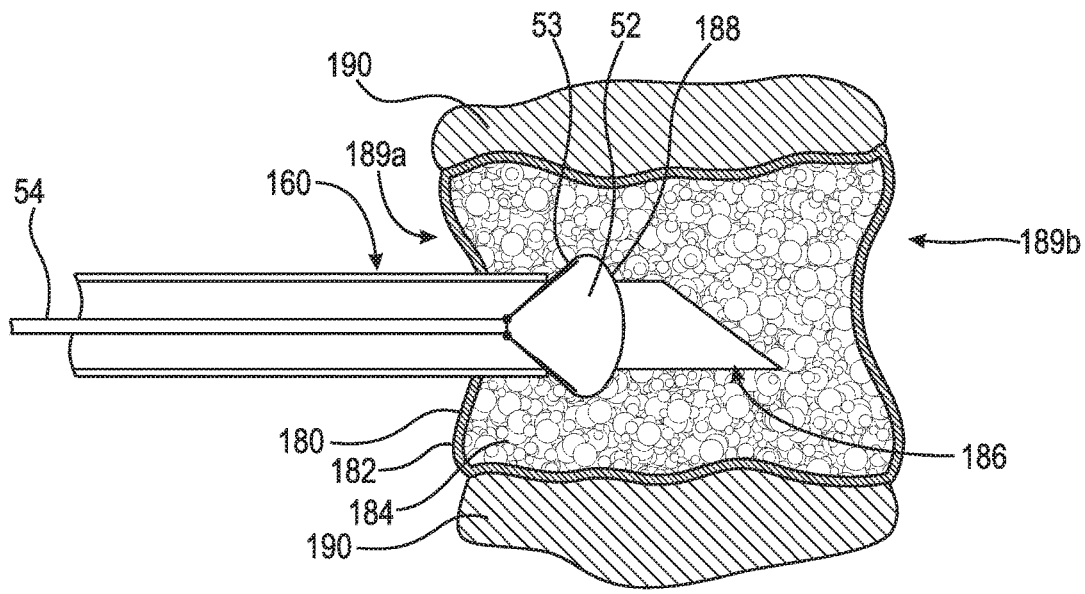
FIG. 16C shows the inflatable balloon anchor positioned inside the cancellous material at the core of the apex vertebra and starting to inflate creating a cavity.
Figure 16D:
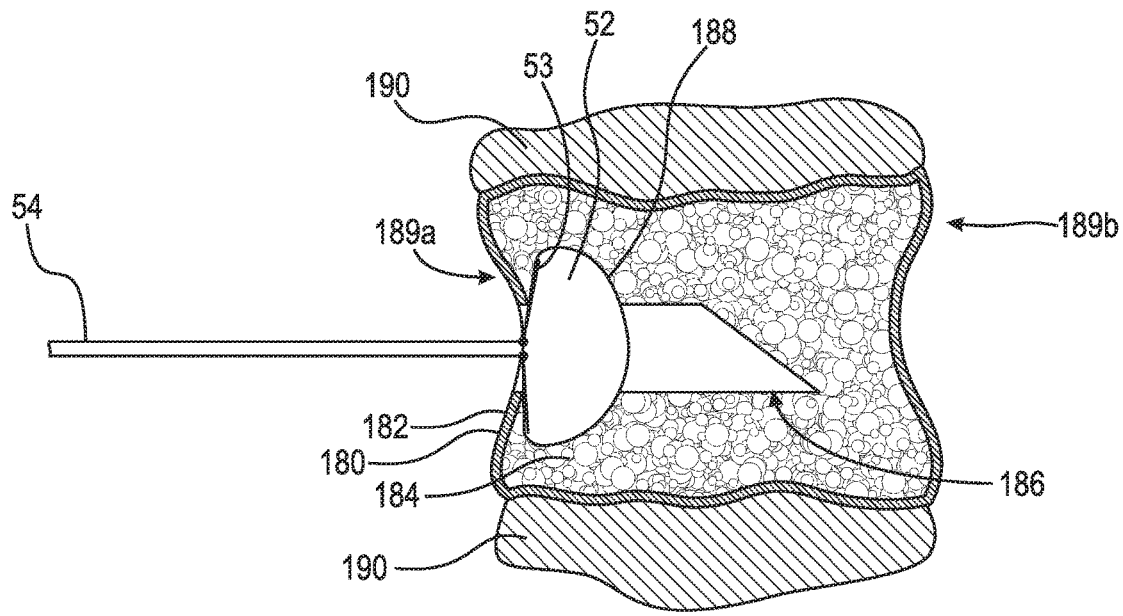
FIG. 16D depicts the inflatable balloon anchor sufficiently inflated and the cavity formed within the apex vertebra.

FIG. 16A is a cross-sectional view of penetrating bone needle 160, including removable stylet 170, line 54, and inflatable balloon anchor 52 therein, inserted into apex vertebra 180, preferably the center thereof, to create hole 186 extending from lateral side 189a. Hole 186 is formed by tapered cutting tip 176. At the same time, cylindrical needle 162 is guided through hole 186. FIG. 16A depicts a second method of attaching inflatable balloon anchor 52 to apex vertebra 180. FIG. 16B shows removable stylet 170 withdrawn from apex vertebra 180 and line 54 and inflatable balloon anchor 52 arranged in cylindrical needle 162. FIG. 16C shows inflatable balloon anchor 52 positioned inside cancellous material 184 at the core of apex vertebra 180 and starting to inflate creating cavity 188. Cylindrical needle 162 is removed from hole 186. Fluid is introduced into inflatable balloon anchor 52 through line 54. Inflatable balloon anchor 52 is inflated and expands radially beyond the boundaries of hole 186 into cancellous material 184 forming cavity 188. As fluid volume increases, the general diameter of inflatable balloon anchor 52 (and thus cavity 188) becomes larger than the diameter of hole 186 in cortical material 182 on lateral side 189a of apex vertebra 180. FIG. 16D depicts inflatable balloon anchor 52 sufficiently inflated and cavity 188 formed within cancellous material 184 of apex vertebra 180. Inflatable balloon anchor 52 is sufficiently inflated when its general diameter is larger than the diameter of hole 186. As such, when line 54 is drawn inflatable balloon anchor 52 interferes with cortical material 82 proximate lateral side 189a of apex vertebra 180. For temporary anchor fixation, water or saline may be used to inflate inflatable balloon anchor 52. Permanent fixation may be achieved with hardenable fluids such as bone cement, methyl methylacrylate (MMA), polymethyl methacrylate (PMMA), or any other suitable material as is known to those having ordinary skill in the art. An absorbable material such as bone putty may also be used. It should be appreciated that inflatable balloon anchor 52 may be a noncompliant or compliant balloon.

Figure 17:
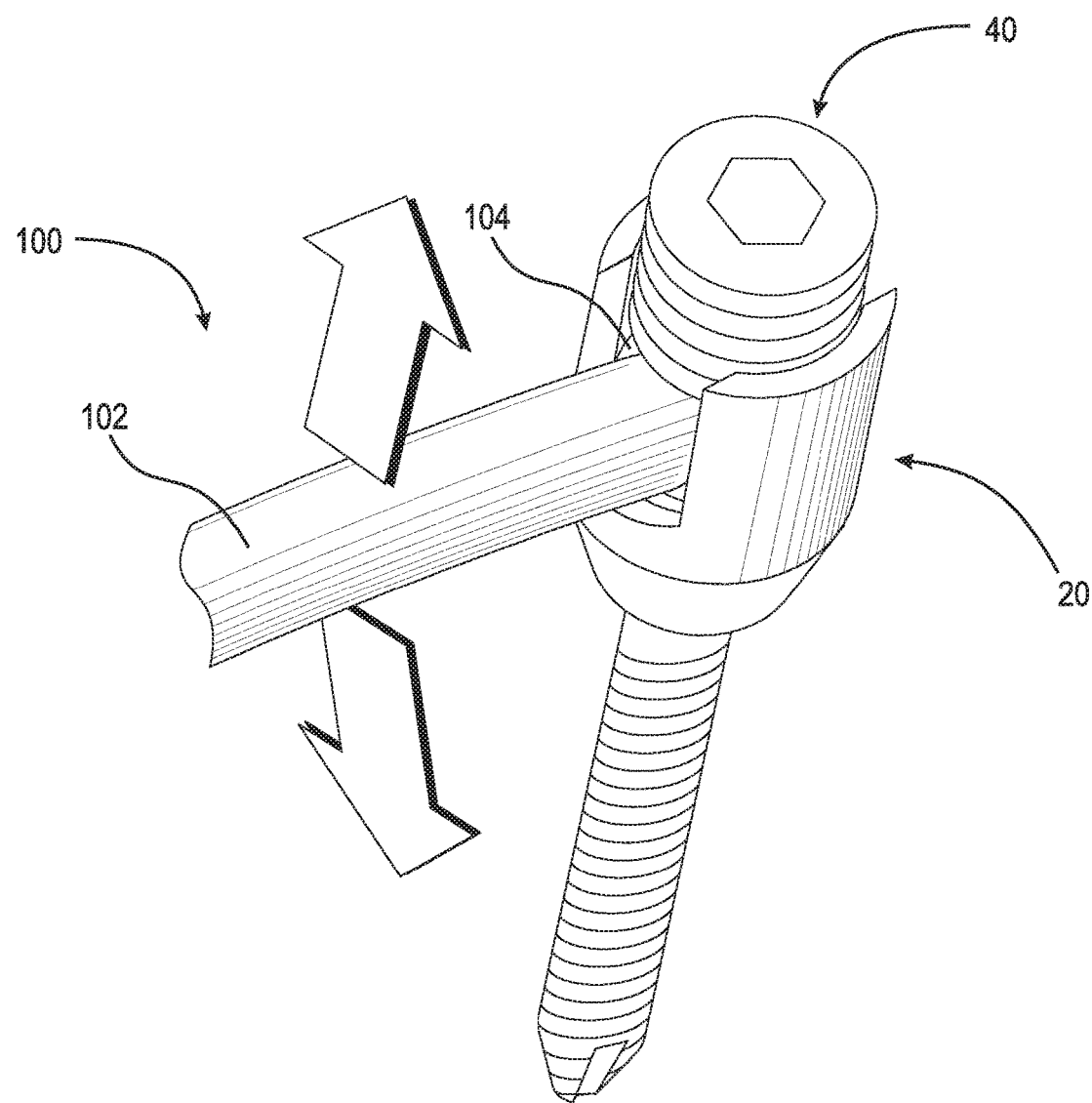
FIG. 17 is an enlarged view taken generally of detail 17 in FIG. 3 of a rod secured to a pedicle screw with a set screw.

FIG. 17 is an enlarged view taken generally of detail 17 in FIG. 3 of rod 100 secured to pedicle screw 20 with set screw 40. End ball 104 is inserted into connector member 26. When fully inserted into connector member 26, end ball 104 is arranged radially within sidewall 28 and abuts against contact surface 27. Set screw 40 is then secured to connector member 26 until contact surface 48 abuts against end ball 104. The spherical curvature of contact surfaces 27 and 48, when end ball 104 is secured therebetween, creates a ball and socket type connection allowing shaft 102 to pivot about end ball 104. Similarly, rod 110 is secured to pedicle screw 30 with set screw 40'. End ball 114 is inserted into connector member 36. When fully inserted into connector member 36, end ball 114 is arranged radially within sidewall 38 and abuts against contact surface 37. Set screw 40' is then secured to connector member 36 until contact surface 48' abuts against end ball 114. The spherical curvature of contact surfaces 37 and 48', when end ball 114 is secured therebetween, creates a ball and socket type connection allowing shaft 112 to pivot about end ball 114.

Figure 18:
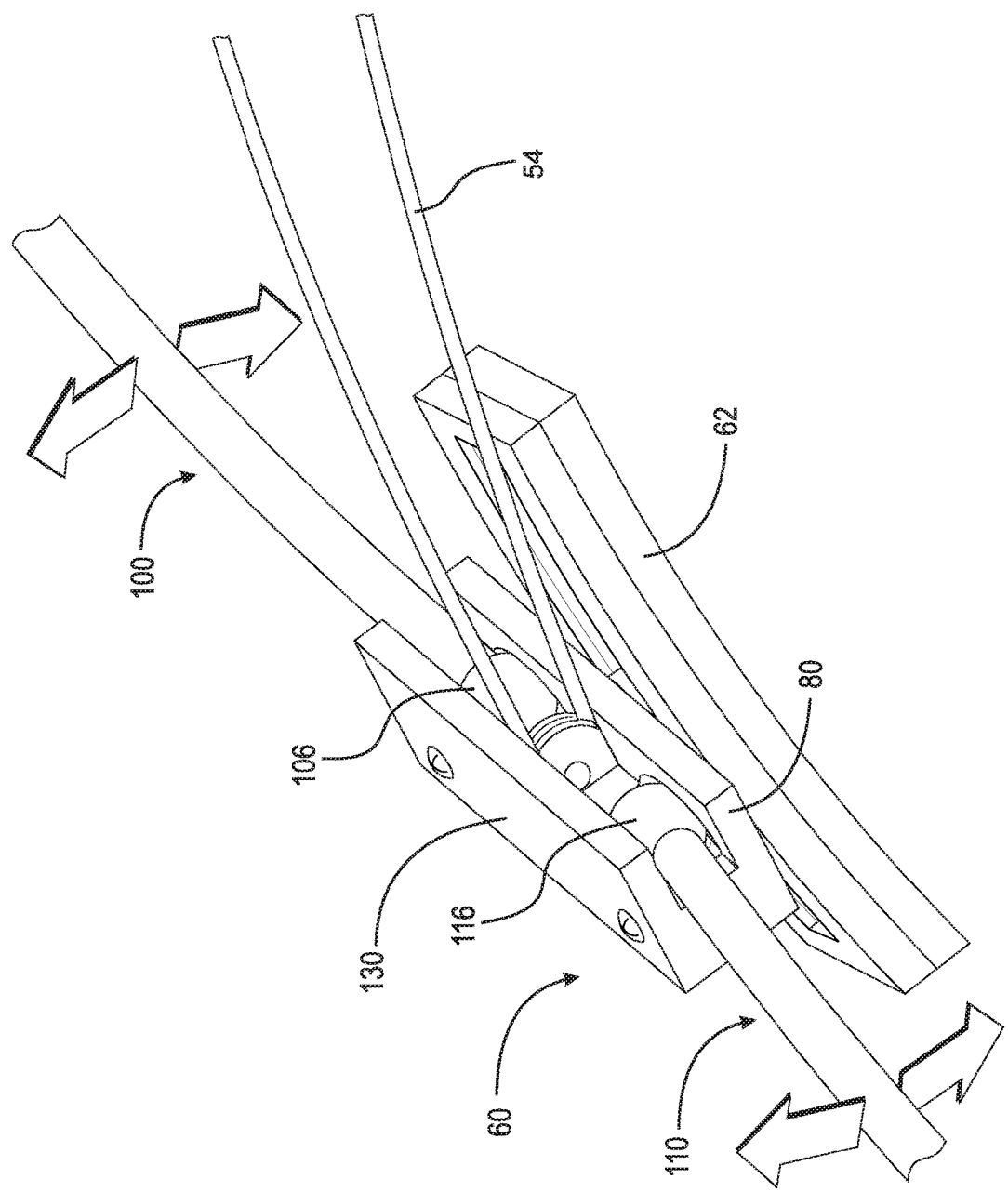
FIG. 18 is an enlarged view taken generally of detail 18 in FIG. 3 of two rods and a pulley secured in the stabilizing plate assembly; and, FIG. 19 is a partial perspective view of the assembly shown in FIG. 3 attached to human spine.

FIG. 18 is an enlarged view taken generally of detail 18 in FIG. 3 rods 100 and 110 and pulley 120 secured in stabilizing plate assembly 60. End ball 106 is inserted into socket 92a. End ball 116 is inserted into socket 92b. Line 54 is aligned in groove 124 and pulley 120 is inserted into groove 90. Locking plate 130 is secured to upper component 80 such that end ball 106 is firmly secured between sockets 92a and 138a, end ball 116 is firmly secured between sockets 92b and 138b, and pulley 120 is secured between grooves 90 and 140. The spherical curvature of sockets 92a and 138a, when end ball 106 is secured therebetween, creates a ball and socket type connection allowing shaft 102 to pivot about end ball 106. The spherical curvature of sockets 92b and 138b, when end ball 116 is secured therebetween, creates a ball and socket type connection allowing shaft 112 to pivot about end ball 116. The radial curvature of grooves 190 and 140 allows pulley 120 to be rotatably fixed substantially about axis of rotation 128, as previously discussed.

Figure 19:
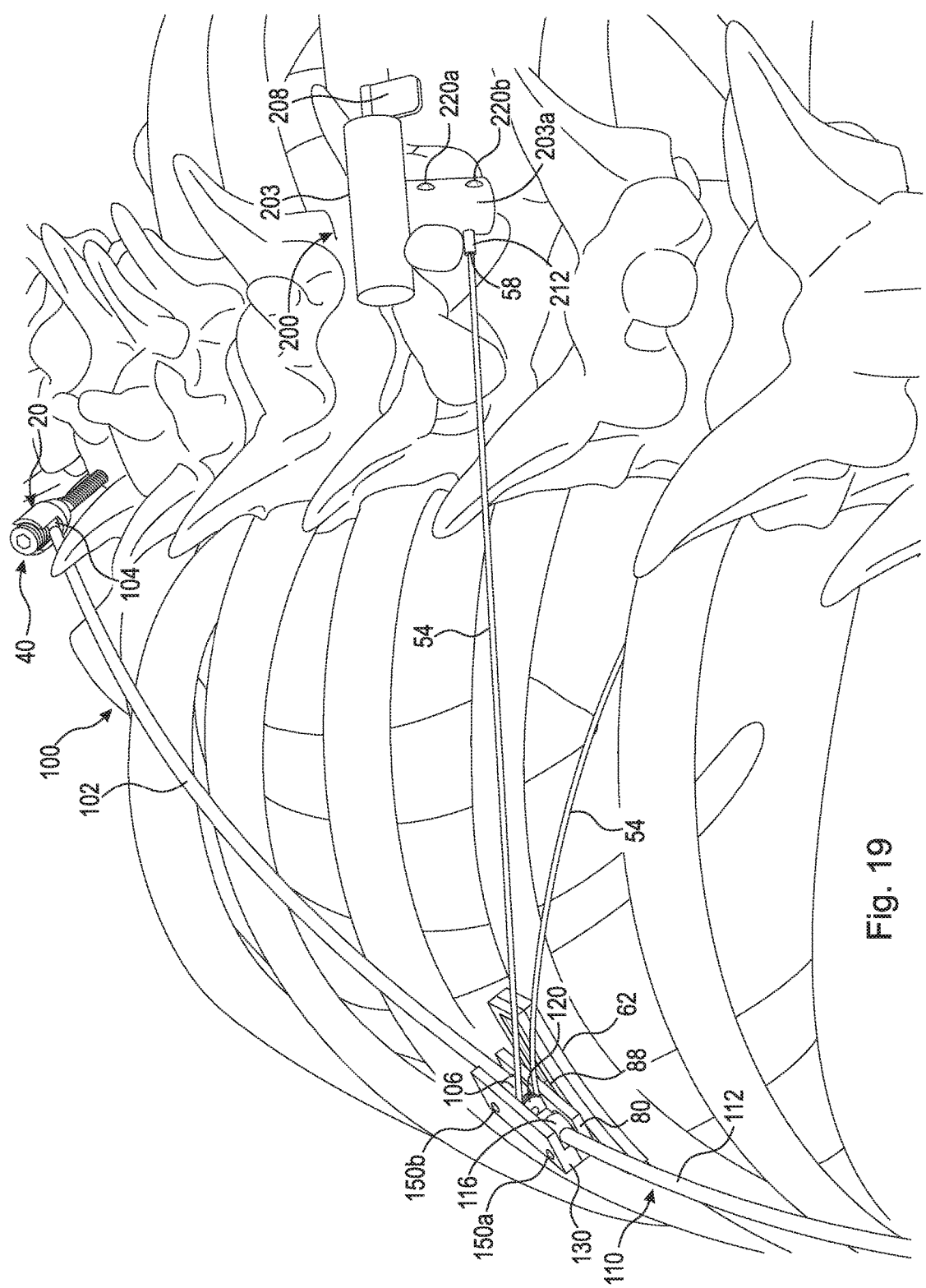

FIG. 19 is a partial perspective view of subcutaneous implantable device 10 shown in FIG. 3 attached to a person. A first incision is made at the top of the spinal curvature, and a second incision is made at the bottom of the spinal curvature. Pedicle screw 20 is inserted through the first incision and secured at the top of the spinal column. Pedicle screw 30 is inserted through the second incision and secured at the bottom of the spinal column.

The following should be read in light of FIGS. 1-19. A third incision is made lateral to apex vertebra 180 of the spinal curvature exposing the underlying ribs. Penetrating bone needle 160 is inserted in the third incision and directed toward the lateral spine. Penetrating bone needle 160 is then gently tapped across apex vertebra 180. Care is taken to avoid the pleura of the lungs. Penetrating bone needle 160 is advanced across the vertebra until end 164 barely protrudes from the contralateral side. Removable stylet 170 is then removed. Inflatable bone anchor 52 is then inserted through cylindrical needle 162 until the tip protrudes on the contralateral side of the vertebra. Inflatable bone anchor 52 is inflated with a material that solidifies within minutes. A stable construct is formed, serving as a strong anchor that can withstand force. Stabilizing plate 60 is inserted through the third incision and is affixed to a rib with screws 74a and 74b (or clamps). Lower component 62 acts as the confluence point of the surgical force vectors, while upper component 80 can mobilize to a limited degree along the rib. Rods 100 and 110 are inserted through the third incision and passed subcutaneously. End ball 104 is secured in pedicle screw 20 via set screw 40. End ball 114 is secured in pedicle screw 30 via set screw 40'. End ball 106 is positioned in socket 92b and end ball 116 is positioned in socket 92a.

A fourth incision is created at apex vertebra 180 of the spinal curvature to allow winding assembly 200 to be affixed to the spinous process of a vertebra, for example, using screws 220a and 220b. Once rods 100 and 110 are in place and winding assembly 200 is secured, line 54 of tensioning member 50 is placed around pulley 120 situated at the center of upper component 80, specifically groove 90, and fed subcutaneously to winding assembly 200. Locking plate 130 is then affixed to upper component 80, for example, using screws 150a and 150b, to secure pulley 120 and capture end balls 106 and 116 of rods 100 and 110, respectively. Line 54 is connected to winding assembly 200 so that when control lever 208 is activated, line 54 gradually winds and tightens. Over time, as line 54 tightens, inflatable balloon anchor 52 pulls apex vertebra 180 of the curve towards stabilizing plate assembly 60, which in turn transfers the vector force to rods 100 and 110. Rods 100 and 110 exert pressure on the upper and lower segments of the spinal curvature, respectively. As the spine gradually straightens, rods 100 and 110 slowly rotate at their connection sites, eventually changing the force exerted from a perpendicular pushing force to a parallel traction force. Meanwhile, upper component 80 and locking plate 130 shift medially to adjust for vector forces. The traction force provided by winding assembly 200 is converted to a pushing force to align the spine. In effect, this subcutaneous implantable device 10 acts as an internal adjustable brace that optimizes force vectors without the problems associated with traditional braces. Once complete alignment is achieved, subcutaneous implantable device 10 remains implanted until skeletal maturity is reached, at which point it can be removed. It should be appreciated that multiple subcutaneous implantable devices can be used to correct spines having multiple curvatures (i.e., spine having multiple curves and thus multiple apexes). It should also be appreciated, that tensioning member 50 can be used for purposes other than gradually aligning a spine. For example, tensioning member 50 can be used to reattach a tendon to a bone.

It will be appreciated that various aspects of the disclosure above and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

REFERENCE NUMERALS

P Person
1 Spinal column
2 Upper curve
3 Lower curve
4 Brace
5 Brace
10 Subcutaneous implantable device
20 Pedicle screw
22 Screw member
24 External threads
26 Connector member
27 Contact surface
28 Side wall
29 Internal threads
30 Pedicle screw
32 Screw member
34 External threads
36 Connector member
37 Contact surface
38 Side wall
39 Internal threads
40 Set screw
42 Radially outward facing surface
44 External threads
46 Screw head
48 Contact surface
40' Set screw
42' Radially outward facing surface
44' External threads
46' Screw head
48' Contact surface
50 Tensioning member
52 Inflatable anchor
53 Array (arms)
54 Line
56 End
58 End
60 Stabilizing plate assembly
62 Lower component
64 Top surface
66 Bottom surface
67 Track
68 Channel
69a Side
69b Side
70 Opening
72a Through-bore
72b Through-bore
74a Screw
74b Screw
80 Upper component
82 First top surface
84 Second top surface
86 Bottom surface
87 Runner
88 Shaft
89 Flange
90 Groove
92a Socket
92b Socket
94a Hole
94b Hole
100 Rod
102 Shaft
104 End ball
106 End ball
110 Rod
112 Shaft
114 End ball
116 End ball
120 Pulley
122 Radially outward facing surface 124 Groove
126 Radially inward facing surface
128 Axis of rotation
130 Locking plate
132 Top surface
134 First bottom surface
136 Second bottom surface
138a Socket
138b Socket
140 Groove
142a Through-bore
142b Through-bore
150a Screw
150b Screw
160 Penetrating bone needle
162 Cylindrical needle
164 End
166 End
168 Handle
170 Removable stylet
172 Cap
174 Cylindrical needle
176 Tapered cutting tip
180 Vertebra
181 Spinous process
182 Cortical (hard) material
184 Cancellous (soft) material
186 Hole
188 Cavity
189a Lateral side
189b Contralateral side
190 Intervertebral disc
200 Winding assembly
202 Ratcheting mechanism
203 Housing
203A Housing
203B Housing
204 Screw
205A Spring
205B Spring
206 Wheel
208 Control lever
208A Rebound board
210 Stem
211 Coil spring
212 Port
216 Ratchet assembly
216A Ratchet gear
216B Ratchet gear
217 Spring
217P Pawl
218a Through-bore
218b Through-bore
220a Screw
220b Screw
230 Motor
232 Receiver
234 Power source
236 Programmable computer

What is claimed is:

1. A subcutaneous implantable device for aligning a spine having a plurality of vertebrae, comprising:
   a stabilizing plate assembly;
   a first rod, including:
      a first end; and,
      a second end pivotably connected to the stabilizing plate assembly;
   a second rod, including:
      a third end; and,
      a fourth end pivotably connected to the stabilizing plate assembly;
   a winding assembly; and,
   a tensioning member including a line, the line having:
      a first end; and,
      a second end secured to the winding assembly;
   wherein the line is connected to the stabilizing plate assembly.

2. The subcutaneous implantable device as recited in claim 1, wherein the tensioning member further comprises an inflatable balloon anchor arranged at the first end.

3. The subcutaneous implantable device as recited in claim 2, wherein the line is a hollow tube arranged to introduce a fluid into the inflatable balloon anchor.

4. The subcutaneous implantable device as recited in claim 3, wherein the fluid comprises a hardenable material.

5. The subcutaneous implantable device as recited in claim 3, wherein the fluid comprises an absorbable material.

6. The subcutaneous implantable device as recited in claim 1, wherein the stabilizing plate assembly comprises:
   a lower component; and,
   an upper component slidingly connected to the lower component.

7. The subcutaneous implantable device as recited in claim 6, further comprising a locking plate secured to the upper component.

8. The subcutaneous implantable device as recited in claim 7, wherein:
   the second end is at least partially spherical forming a ball-and-socket joint with the upper component and the locking plate; and,
   the fourth end is at least partially spherical forming a ball-and-socket joint with the upper component and the locking plate.

9. The subcutaneous implantable device as recited in claim 7, wherein the second end and the fourth end are pivotably secured between the locking plate and the upper component.

10. The subcutaneous implantable device as recited in claim 7, further comprising a pulley rotatably secured between the locking plate and the upper component, wherein the line engages the pulley.

11. The subcutaneous implantable device as recited in claim 10, wherein:
    the upper component comprises a first groove;
    the locking plate comprises a second groove; and,
    the pulley is at least partially arranged in the first and second groove.

12. The subcutaneous implantable device as recited in claim 1, further comprising:
    a first pedicle screw; and,
    a second pedicle screw;
    wherein the first end is pivotably secured to the first pedicle screw forming a first pivot connection and the third end is pivotably secured to the second pedicle screw forming a second pivot connection.

13. The subcutaneous implantable device as recited in claim 12, wherein:
    the first end is at least partially spherical forming a ball-and-socket joint with the first pedicle screw and a first set screw; and,
    the third end is at least partially spherical forming a ball-and-socket joint with the second pedicle screw and a second set screw.

14. The subcutaneous implantable device as recited in claim 12, wherein:
the first pivot connection is arranged to be secured to a first vertebra of the spine;
the second pivot connection is arranged to be secured to a second vertebra of the spine;
the stabilizing plate assembly is arranged to be secured to a rib of the rib cage; and
the winding assembly is arranged to be connected to a third vertebra of the spine.

15. The subcutaneous implantable device as recited in claim 1, wherein the winding assembly comprises an actuator operatively arranged to create tension on the line.

16. The subcutaneous implantable device as recited in claim 15, wherein the actuator comprises a subcutaneous control lever activated by an applied force.

17. The subcutaneous implantable device as recited in claim 15, wherein the actuator comprises a motor activated by wireless communication.

18. The subcutaneous implantable device as recited in claim 17, wherein the motor further comprises a programmable computer.

\* \* \* \* \*